US006881732B2

(12) United States Patent
Winchell

(10) Patent No.: US 6,881,732 B2
(45) Date of Patent: Apr. 19, 2005

(54) NEUROPROTECTION AND CARDIOPROTECTION AFFORDED BY CHELATORS WITH HIGH AFFINITY AND SPECIFICITY FOR CATIONS OF FIRST TRANSITION SERIES ELEMENTS

(75) Inventor: Harry S. Winchell, Lafayette, CA (US)

(73) Assignees: Chelator LLC, Concord, CA (US); Concat, Ltd., Concord, CA (US)

( * ) Notice: Subject to any disclaimer, the term of this patent is extended or adjusted under 35 U.S.C. 154(b) by 0 days.

(21) Appl. No.: 10/172,766

(22) Filed: Jun. 13, 2002

(65) Prior Publication Data

US 2004/0006055 A1 Jan. 8, 2004

(51) Int. Cl.$^7$ .................. A61K 31/33; A61K 31/675
(52) U.S. Cl. ............................ 514/183; 514/79
(58) Field of Search .................... 514/79, 183

(56) References Cited

U.S. PATENT DOCUMENTS

| | | | |
|---|---|---|---|
| 5,380,515 A | | 1/1995 | Winchell et al. |
| 5,854,287 A | * | 12/1998 | Weglicki .................... 514/569 |
| 5,874,573 A | | 2/1999 | Winchell et al. |
| 6,264,966 B1 | | 7/2001 | Winchell et al. |
| 2001/0033854 A1 | | 10/2001 | Johnson et al. |
| 2001/0036964 A1 | | 11/2001 | Clarkson et al. |

OTHER PUBLICATIONS

The Merck Manual of Diagnosis and Therapy, 14$_{th}$ ed., (1982), pp 910–915.*

Blot, W.J., et al., "Nutrition Intervention Trials in Linxian, China: Supplementation with Specific Vitamin/Mineral Combinations, Cancer Incidence, and Diseaese–Specific Mortality in the General Population," *Journal of the National Cancer Institute*, 1993, pp. 1483–1492, vol. 85, No. 18.

Omenn, G.S., et al., "Effects of a Combination of Beta Carotene and Vitamin A on Lung Cancer and Cardiovascular Disease," *New England Journal of Medicine*, 1996, pp. 1150–1155, vol. 334, No. 18.

Hennekens, C.H., et al., "Lack of Effect of Long–Term Supplementation with Beta Carotene on the Incidence of Malignant Neoplasms and Cardiovascular Disease," New England Journal of Medicine, 1996, pp. 1145–1149, vol. 334, No. 18.

Grennberg, E.R., et al., "Mortality Associated with Low Plasma Concentration of Beta Carotene and the Effect of Oral Supplementation," *JAMA*, 1996, pp. 699–703, vol. 275, No. 9.

Gilgun–Sherkl, Y., et al., "Antioxidant Therapy in Acute Central Nervous System Injury: Current State,"; 2002, *Pharm. Rev.* vol. 54, pp. 271–284.

Heart Protection Study Collaborative Group, "MRC/BHF Heart Protection Study of antioxidant vitamin supplementation in 20536 high–risk individuals: a randomized placebo–controlled trial,"; 2002, *The Lancet* vol. 360, pp. 23–33.

* cited by examiner

*Primary Examiner*—Raymond J. Henley, III
(74) *Attorney, Agent, or Firm*—M. Henry Heines; Townsend and Townsend and Crew, LLP

(57) ABSTRACT

Compounds that demonstrate chelation affinity and selectivity for first transition series elements are administered to patients suffering from such conditions as ischemia, prolonged seizures and trauma to provide neuroprotection, cardioprotection, or both. These compounds when administered form complexes with chelatable iron and copper cations and thereby mitigate the ability of these cations to catalyze Haber-Weiss reactions that form toxic hydroxy free radicals that cause tissue injury. These compounds also form complexes with chelatable zinc cations thereby inhibiting the cytotoxicity associated with excess chelatable zinc.

7 Claims, No Drawings

NEUROPROTECTION AND CARDIOPROTECTION AFFORDED BY CHELATORS WITH HIGH AFFINITY AND SPECIFICITY FOR CATIONS OF FIRST TRANSITION SERIES ELEMENTS

BACKGROUND OF THE INVENTION

1. Field of the Invention

This invention resides in the field of chelating agents and medical uses of such agents. This invention also resides in the field of treatments for ischemia, seizures and trauma. All literature and patent citations in this specification are hereby incorporated herein by reference.

2. Description of the Prior Art

Iron and copper cations are known to catalyze hydroxy free radical formation in Haber-Weiss pathways. Hydroxy free radicals themselves are known to produce tissue damage. Iron and copper cations are released from tissues during ischemia and in association with a variety of disease processes.

Attempts to mitigate the catalytic effectiveness of iron and copper cations by administering iron chelating siderophores such as deferoxamine to form complexes with these cations have not been unequivocally successful in inhibiting tissue damage from hydroxy free radicals in vivo. Siderophores such as deferoxamine are poor chelators for copper cations. Although present in the body in much lower concentrations than iron, copper is far more active than iron in catalyzing hydroxy free radical formation via Haber-Weiss pathways.

It is further known that complexes of iron with many chelating agents retain the ability of iron to catalyze hydroxy free radical formation in Haber-Weiss pathways. Iron complexed by the chelator ethylene diamine tetra acetic acid (EDTA) is typically more active in catalyzing free radical formation in Haber-Weiss pathways at near neutral pH than is uncomplexed iron. Iron complexes of N,N,N',N'-tetrakis (2-pyridylmethyl)ethylene diamine (TPEN) and hydrolyzed forms of 4,4'-(1-methyl-1,2,-ethanediyl)bis-2,6-piperazinedione (Razoxane) also are active in catalyzing free radical formation in Haber-Weiss pathways.

It is also known that zinc cations are co-released with glutamate from synaptosomes of nervous system cells that employ glutamate as a chemical messenger. Normally such zinc released in the nerve synapse is rapidly re-incorporated into synaptosomes. The zinc released from synaptosomes as a result of ischemia, prolonged seizures and brain injury accumulates in the extracellular fluid surrounding nerve cell bodies. When excess zinc enters the cell body, the zinc can initiate cell death by apoptosis and necrosis. Since siderophores such as deferoxamine have low affinity for zinc cations, their use has not unequivocally provided neuroprotection.

It is still further known that metal cations such as $Ca^{+2}$ that are not first transition series elements perform important functions in the body. Such metal cations can compete with cations of first transition series elements for chelation by a chelator that has a high affinity for $Ca^{+2}$ and thereby interfere with the chelation of first transition series cations by the chelator. Moreover, chelation of cations such as $Ca^{+2}$ can impair the normal functions of these cations in the body.

SUMMARY OF THE INVENTION

It has now been discovered that chelators that form complexes with at least one species of cations of the first transition series elements iron, copper, and zinc in which the complexes have a thermodynamic equilibrium dissociation constant of $10^{-18}$ or less and that form complexes with $Ca^{+2}$ with thermodynamic equilibrium dissociation constants of $10^{-11}$ or more are effective pharmaceutical agents in the treatment of conditions such as ischemic stroke, seizure, and trauma, including heart attack and arrhythmia. Chelators (also referred to herein as "ligands") with high affinity for both iron and copper cations provide robust cardioprotection to an unexpectedly high degree, while chelators with high affinity for iron, copper, and zinc, provide neuroprotection to an unexpectedly high degree. In the practice of this invention, the chelators are administered free of iron, zinc and copper cations and therefore available to form complexes with these cations upon contact with these cations in the physiological system. The pharmaceutical compositions of this invention thus contain as active agents the chelators not complexed with iron, copper or zinc cations.

DETAILED DESCRIPTION OF THE INVENTION AND PREFERRED EMBODIMENTS

This invention resides in methods for providing neuroprotection, cardioprotection, or both, to a patient suffering from conditions that give rise to an increase in chelatable levels of first transition series elements. The protection is achieved by administering to a patient a chelating agent (or ligand) which is capable of complexing first transition series elements.

Among the ligands used in the practice of the present invention are those represented by the following Formulas I through IV:

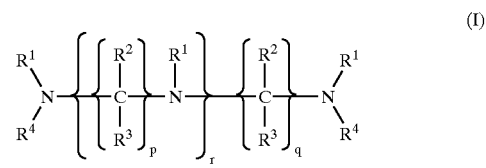

(I)

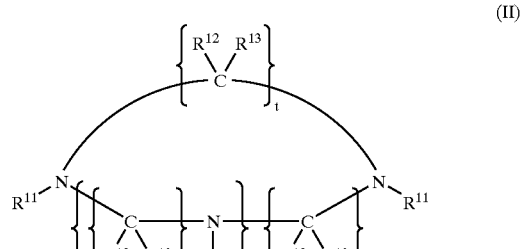

(II)

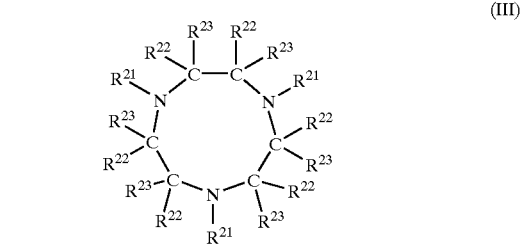

(III)

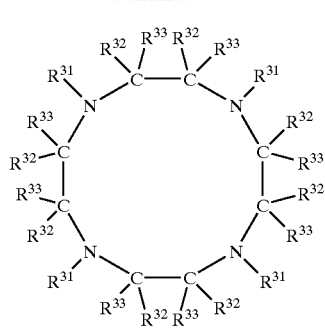

(IV)

In Formulas I through IV, $R^1$, $R^2$, $R^3$, and $R^4$ may be the same or different on any single molecule, and the same is true for $R^{11}$, $R^{12}$, and $R^{13}$, for $R^{21}$, $R^{22}$, and $R^{23}$, and for $R^{31}$, $R^{32}$, and $R^{33}$. Each of these symbols ($R^1$ through $R^{33}$) represents H, alkyl, alkenyl, aryl, arylalkyl, alkoxy, alkylthio, alkenoxy, alkenylthio, aryloxy, arylthio, alkyl interrupted by one or more oxa (—O—), alkenyl interrupted by one or more oxa (—O—), alkyl interrupted by one or more thia (—S—), alkenyl interrupted by one or more thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups that do not interfere with complexation and that they are not combined in a manner that results in a chemically unstable configuration. The alkyl, alkenyl and aryl groups, or portions of groups, in the foregoing list can also be substituted with one or more halogen atoms.

In addition to the radicals and radical subclasses listed above, $R^1$, $R^4$, $R^{11}$, $R^{21}$ and $R^{31}$ are further defined to include:

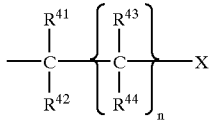

(V)

In Formula V, $R^{41}$, $R^{42}$, and $R^{43}$ may be the same or different on any single radical, and are defined as H, alkyl, alkenyl, aryl, arylalkyl, alkoxy, alkylthio, alkenoxy, alkenylthio, aryloxy, arylthio, alkyl interrupted by one or more oxa (—O—), alkenyl interrupted by one or more oxa (—O—), alkyl interrupted by one or more thia (—S—), alkenyl interrupted by one or more thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups that do not interfere with complexation and that they are not combined in a manner that results in a chemically unstable configuration. Here again, the alkyl, alkenyl and aryl groups, or portions of groups, in the foregoing list can also be substituted with one or more halogen atoms. $R^{44}$ in Formula V is defined as H, hydroxy, amino, alkyl, alkyl interrupted by oxa (—O—), alkoxy, aryl, aryloxyalkyl, alkoxyaryl, or any of these groups in which the alkyl and aryl portions are substituted with one or more halogen atoms. Again, the groups are selected such that they do not interfere with complexation and are not combined in a manner that results in a chemically unstable configuration.

The index n is either zero or 1.
The symbol X represents any of the following groups:

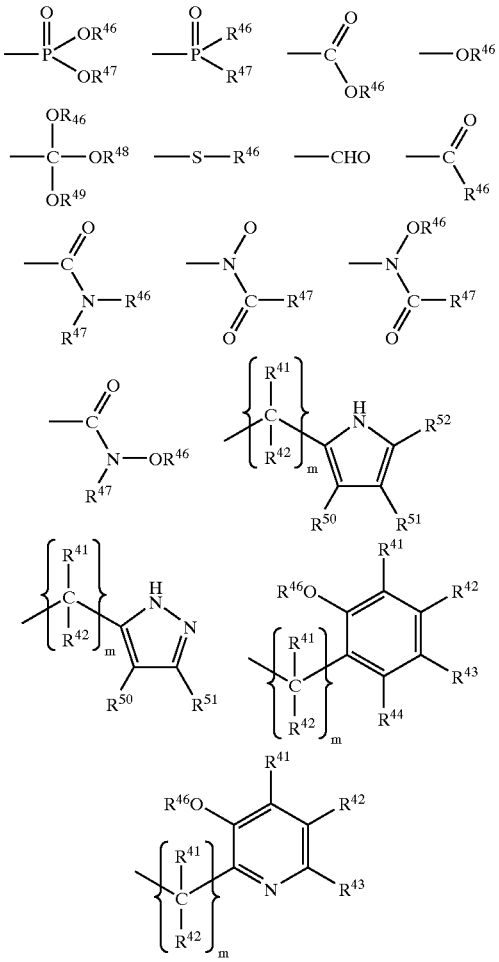

In these formulas, $R^{41}$, $R^{42}$, $R^{43}$, and $R^{44}$ may be the same or different on any single radical, and each has the same definition as that given above for $R^{41}$, $R^{42}$, and $R^{43}$.

The groups $R^{46}$, $R^{47}$, $R^{48}$ and $R^{49}$ may be the same or different on any single radical, and are each defined as H, or alkyl or aryl groups that do not interfere with complexation. $R^{46}$ and $R^{47}$ may further be combined as a single divalent group, thereby forming a ring structure. $R^{48}$ and $R^{49}$ are further defined to include alkoxy, alkyl interrupted by oxa (—O—), aryloxyalkyl, and alkoxyaryl, combine in a manner that results in a chemically stable configuration. All alkyl and aryl groups in this paragraph, including alkyl and aryl portions of groups, are optionally substituted with one or more halogen atoms.

The groups $R^{50}$, $R^{51}$, and $R^{52}$ may be the same or different on any single radical, and are each defined as H, alkyl, alkenyl, aryl, arylalkyl, alkyloxy, alkylthio, alkenyloxy, alkenylthio, aryloxy, arylthio, aminoalkyl, aminoalkenyl, aminoaryl, aminoarylalkyl, hydroxyalkyl, hydroxyalkenyl, hydroxyaryl, or hydroxyarylalkyl.

The index m is an integer which is either 1, 2, or 3.

Returning to Formulas I through IV, further variations within the scope of this invention are as follows:

(1) Internal cyclizations within these formulas at the nitrogen atoms, formed by joining together any two of the $R^1$ and $R^4$ groups in Formula I, any two of the $R^{11}$ groups in Formula II, any two of the $R^{21}$ groups in Formula III, or any two of the $R^{31}$ groups in Formula IV, as a single divalent group bridging the two nitrogen atoms, the single divalent group having the formula

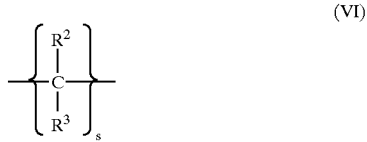

(VI)

in which $R^2$ and $R^3$ are as defined above, and s is at least 2, preferably 2 or 3;

(2) Dimers or other two-molecule combinations of Formulas I through IV (the molecules being the same or different), formed by bridging the molecules together through one or more divalent groups of Formula VI (as defined above) substituted for any one or two of the $R^{11}$ groups in Formula II, any one or two of the $R^{21}$ groups in Formula II, or any one or two of the $R^{31}$ groups in Formula IV;

(3) Internal cyclizations at common carbon atoms within these formulas to form homocyclic rings, by joining one or more of the $R^2$, $R^{12}$, $R^{22}$, or $R^{32}$ groups to one or more of the $R^3$, $R^{13}$, $R^{23}$, or $R^{33}$ groups at the same carbon atom, as a single divalent group of Formula VI (as defined above), and forming one or more such homocyclic rings per structure in this manner; and (4) Internal cyclizations involving two carbon atoms separated by a nitrogen atom within these formulas to form heterocyclic rings, by joining any two adjacent $R^2$ groups in Formula I, any two adjacent $R^{12}$ groups in Formula II, any two adjacent $R^{22}$ groups in Formula II, or any two adjacent $R^{32}$ groups in Formula IV, as a single divalent group of Formula VI (as defined above) and forming one or more such heterocyclic rings per structure in this manner.

In Formula I, the subscripts p and q may be the same or different, and are each either 2 or 3. The subscript r is 0 to 4, inclusive, with the proviso that in the absence of a ring structure r is 1 to 4, inclusive. Preferably, r is 1 or 2.

In Formula II, t, u, and v may be the same or different, and are each either 2 or 3. The value of w is at least 1, more preferably 1 to 4, inclusive, still more preferably 1 to 3, inclusive, and most preferably either 1 or 2.

The terms used in connection with these formulas have the same meaning here as they have in the chemical industry among those skilled in the art. The term "alkyl" thus encompasses both straight-chain and branched-chain groups and includes both linear and cyclic groups. The term "alkenyl" refers to unsaturated groups with one or more double bonds and includes both linear and cyclic groups. The term "aryl" refers to aromatic groups or one or more cycles.

For all such groups, those which are useful in the present invention are those that do not impair or interfere with the formation of the chelate complexes. Within this limitation, however, the groups may vary widely in size and configuration. Preferred alkyl groups are those having 1 to 8 carbon atoms, with 1 to 4 carbon atoms more preferred. Prime examples are methyl, ethyl, isopropyl, n-propyl, and tert-butyl. Preferred aryl groups are phenyl and naphthyl, particularly phenyl. Preferred arylalkyl groups are phenylethyl and benzyl, and of these, benzyl is the most preferred. Preferred cycloalkyl groups are those with 4 to 7 carbon atoms in the cycle, with cycles of 5 or 6 carbon atoms particularly preferred. Preferred halogen atoms are chlorine and fluorine, with fluorine particularly preferred.

One particularly preferred subclass of compounds within Formula I are those in which $R^1$ is alkyl, alkenyl, aryl, arylalkyl, or cycloalkyl, substituted at the i-position with hydroxy. Further preferred are compounds in which one or more, and preferably two or more, of such groups ($R^1$, $R^{11}$, $R^{21}$ and $R^{31}$) on the same formula are substituted at the β-position with hydroxy. Still further preferred are compounds in which the β-hydroxy substituted groups are further substituted at the β-position with at least one hydroxymethyl, alkoxymethyl, alkenoxymethyl, aryloxymethyl, or combinations thereof, all of which may also be further substituted with halogen. Included among these are compounds of Formula III in which one or more of the $R^{21}$ groups are substituted at the β-position with hydroxy and also with hydroxymethyl, alkoxymethyl, alkenoxymethyl, or aryloxymethyl, all of which may also be further substituted with halogen, and the $R^{22}$ and $R^{23}$ groups are all hydrogen atoms.

Certain specific groups for $R^1$, $R^{11}$, $R^{21}$, and $R^{31}$ are particularly preferred. These are 2-hydroxy(2,2-diisopropoxymethyl)ethyl and (3-hydroxy-6,6,7,7-tetramethyl-1,5-dioxacyclohept-3-yl)methyl.

Preferred ligands for use in the practice of this invention are those with molecular weights that do not exceed 2000. More preferred are those whose molecular weight is from about 200 to about 1800, and the most preferred are those whose molecular weight is from about 400 to about 1100.

Where indicated, physiologically or pharmacologically compatible salts of the ligands that have an excess of acidic groups are formed by neutralizing the acidic moieties of the ligand with physiologically or pharmacologically compatible cations from corresponding inorganic and organic bases and amino acids. Examples are alkali and alkaline earth metal cations, notably sodium, calcium and magnesium. Combinations of these cations can also be used. Further examples are primary, secondary and tertiary amines, notably ethanolamine, diethanolamine, morpholine, glucamine, N,N-dimethylglucamine, and N-methylglucamine (commonly referred to as "megluime"). Examples of amino acid cations are lysines, arginines, and ornithines.

Similarly, physiologically or pharmacologically compatible salts of those ligands that have an excess of basic groups are formed by neutralizing the basic moieties of the ligand with physiologically or pharmacologically compatible anions from corresponding inorganic and organic acids. Examples are halide ions, notably chloride. Further examples are sulfates, bicarbonate, acetate, pyruvate and other inorganic and organic acids.

The chelators used in the practice of this invention form complexes with cations of first transition series metals of which iron, copper and zinc are a primary interest. In the practice of this invention, the chelators are administered in a form that will allow or promote complexation with these cations in the physiological system. This form may either be the non-complexed chelators, i.e., the ligands themselves free of any metal cations, or complexes of the chelators with metal cations that have a lower affinity for the chelators than do the first transition series metal cations and are therefore susceptible to trans-complexation with first transition series metal cations in the physiological system. Complexes of the chelators with calcium ion, for example, will undergo trans-complexation to replace the calcium ion with a first transition series metal cation, and will therefore be approximately as effective a therapeutic agent as the chelators themselves in cation-free form. Accordingly, preferred chelators used in the practice of this invention are those that form a complex with iron, copper or zinc with a thermodynamic equilibrium dissociation constant of about $10^{-18}$ or less and that form a complex with calcium with a thermodynamic equiplibrium dissociation constant of $10^{-11}$ or more.

The first transition series metals that form complexes with the chelators of this invention can assume any of the various oxidation states in which these metals are known to exist in ionic or combined form. Thus, for example, the chelators of this invention can form complexes with ferric ion or ferrous ion, and cupric ion or cuprous ion.

Pharmaceutical compositions containing the ligands described herein are prepared and administered according to standard techniques. The pharmaceutical compositions can be administered parenterally, i.e., intraarticularly, intravenously, subcutaneously, or intramuscularly. Suitable formulations for use in the present invention are found in *Remington's Pharmaceutical Sciences*, Mack Publishing Company, Philadelphia, Pa., 17th ed. (1985).

The ligands can be administered intravenously. This invention thus provides compositions fore intravenous administration which comprise a solution of the non-complexed ligand in an pharmacologically acceptable carrier, preferably an aqueous carrier. A variety of aqueous carriers can be used, such as water, buffered water, 0.9% isotonic saline, and the like. These compositions can be sterilized by conventional, well known sterilization techniques, or may be sterile filtered. The resulting aqueous solutions can be packaged for use as is, or lyophilized, and if lyophilized, the lyophilized preparation will be combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, calcium chloride, sorbitan monolaurate, and triethanolamine.

The concentration of the active agent in the pharmaceutical composition can vary widely, i.e., from less than about 0.05%, usually at or at least about 2–5% to as much as 10 to 30% by weight, and will be selected primarily by fluid volumes, viscosities, and other such parameters, in accordance with the particular mode of administration selected.

The methods of this invention can be performed on a variety of subjects, preferably mammalian subjects such as humans, non-human primates, and dogs, cats, cattle, horses, goats, and sheep, i.e., domestic animals and livestock.

The foregoing description and the following examples are offered primarily for illustration and are not intended to limit scope of the invention. It will be readily apparent to those of ordinary skill in the art that the substances, compositions, methods of formulation, and methods of administration can be further modified or substituted in various ways without departing from the spirit and scope of the invention.

EXAMPLE 1

This example illustrates the synthesis of chelators (ligands) which are useful in the present invention. Section 1.1 illustrates the synthesis of polyaza bases. Section 1.2 illustrates the synthesis of alkylating groups. Section 1.3 illustrates the preparation of chelating agents from alkylation of polyaza bases.

In all examples reactions were carried out in common solvents, compounds were purified by routine methodology and identity was established by proton NMR. In some cases identity was further verified by elemental analysis, mass spectroscopy, C-13 or P-31 NMR, or by synthesis of the identical compound by an independent alternate synthesis route.

1.1 Synthesis of Polyaza Bases

Ethylene diamine (1.1.0), diethylene triamine (1.1.1), triethylenetetramine (1.1.2), 1,4,7-triazacyclononane (1.1.3), 1,4,7,10-tetraazacyclododecane (1.1.4), 1,4,8,11-tetraazacyclotetradecane (1.1.5), and 1,5,9,13-tetraazacyclohexadecane (1.1.6) and the corresponding hydrohalide salts were either obtained from commercial sources or were synthesized employing established methods and were used directly in the syntheses of chelators (ligands) described in section 1.3. Additional polyaza bases were synthesized as described herein.

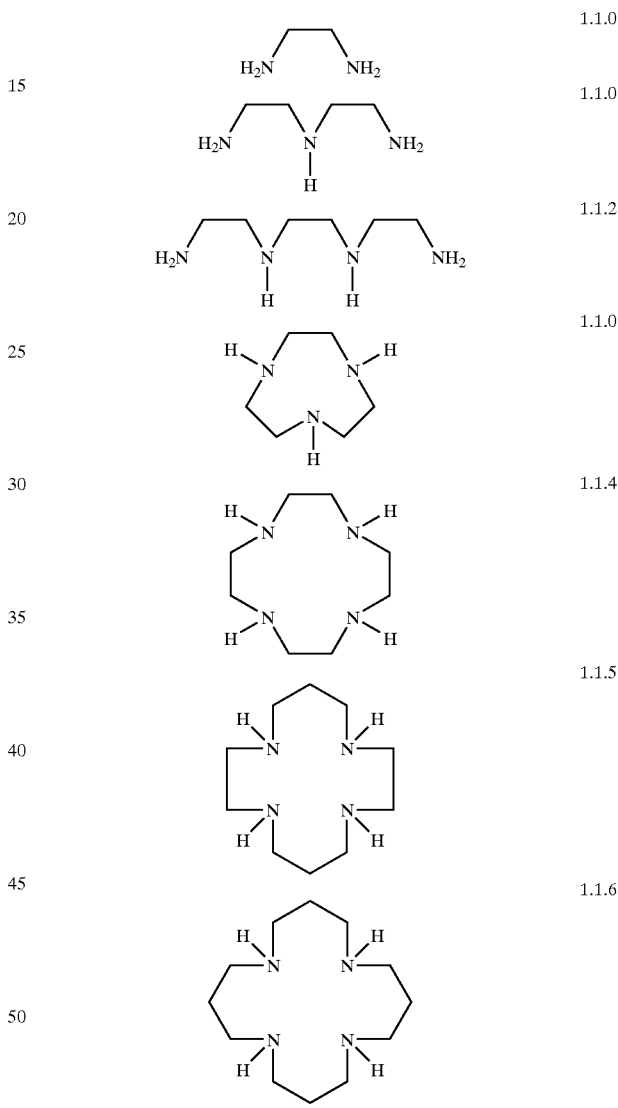

1.1.7: 2,6-Diethyl-1,4,7-triazacyclononane trihydrobromide 2-(p-Toluenesulfonylamino)-1-(p-toluenesulfonyloxy) butane (1.1.8) and ammonium hydroxide were reacted to form 2-(p-toluenesulfonamino)-1-aminobutane (1.1.9). This was reacted with 2-(p-toluenesulfonylamino)-1-(p-toluenesulfonyloxy)butane (1.1.8) and potassium carbonate. The 3,7 bis(p-toluenesulfonylamino)-5-azanonane (1.1.10) product was purified by chromatography and reacted with p-toluenesulfonyl chloride to obtain the corresponding tri-p-toluenesulfonyl compound 3,7 bis(p-toluenesulfonylamino)-5-(p-toluenesulfonyl-5-azanonane (1.1.11). This was purified by chromatography and reacted with 2.2 equivalents of sodium amide in DMF and then with 1,2-di(p-toluene-sulfonyloxy)ethane (1.1.12). The 2,6-diethyl-1,4,7-tris(p-toluenesulfonyl) triazacyclononane (1.1.13) that was obtained following purification was heated in a solution of HBr in acetic acid to remove the p-toluenesulfonyl groups and form the titled compound (1.1.7).

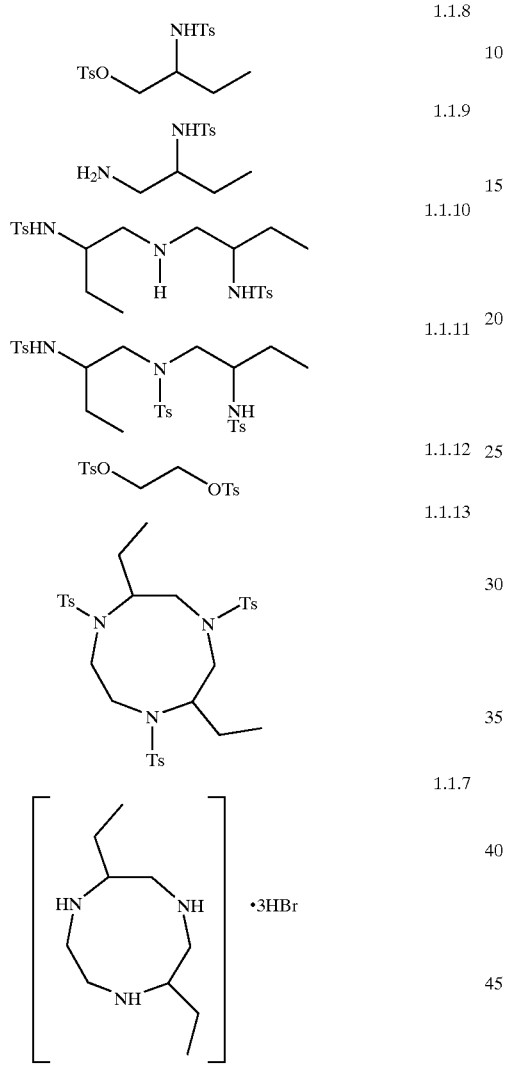

1.1.14: 1,4,7-Triazabicyclo[7.4.0]tridecane Trihydrobromide 1,2-trans-bis(p-Toluenesulfonylamino)cyclohexane (1.1.15) was treated with NaH in DMSO. 1-(p-Toluenesulfonylamino)-2-(p-toluenesulfonyl) ethane (1.1.16) was added to obtain 1-(p-toluenesulfonylamino)-2-[N-p-toluenesulfonyl-N-(2-p-toluenesulfonylaminoethyl)] aminocyclohexane (1.1.17). This was separated and reacted with NaH and 1,2-di(p-toluenesulfonyloxy)ethane (1.1.12) was added. The 2,3-butano-N,N,',N"-tris(p-toluenesulfonyl)-1,4,7-triazacyclononane (1.1.18) obtained was purified by chromatography. The p-toluenesulfonyl groups were removed by reaction in HBr/acetic acid and the 2,3-butano-1,4,7-triazacyclononane trihydrobromide (1.1.14) product precipitated from solution as the hydrobromide salt.

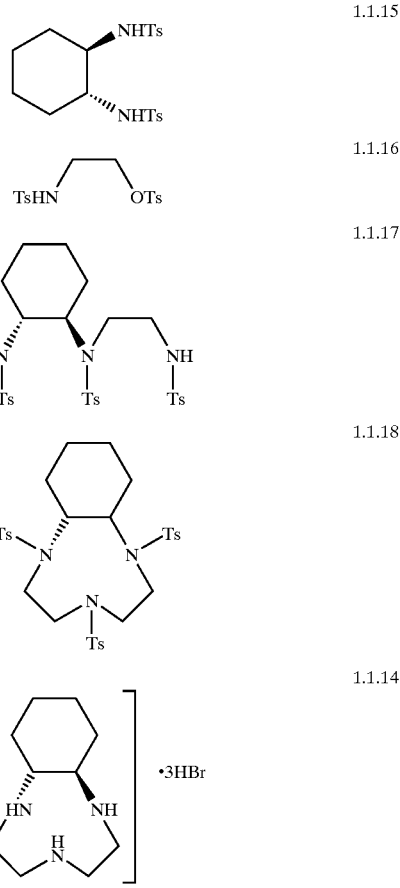

1.1.19: 1,3-Bis (1,4,7-triazacyclononane) propane

N,N'-bis(p-Toluenesulfonyl)-1,4,7-triazacyclononane (1.1.20) was prepared by reacting (1.1.3) with two equivalents of p-toluenesulfonyl chloride. Two equivalents of N,N'-bis(p-toluenesulfonyl)-1,4,7-triazacyclononane (1.1.20) hydrobromide were reacted with one equivalent of 1,3-diiodopropane in acetonitrile with excess potassium carbonate. 1,3-bis[N,N'-bis(p-Toluenesulfonyl)-1,4,7-triazacyclononane propane (1.1.21) was isolated and purified by chromatography. The p-toluene-sulfonyl groups were removed using sulfuric acid and HBr to yield the title compound (1.1.19).

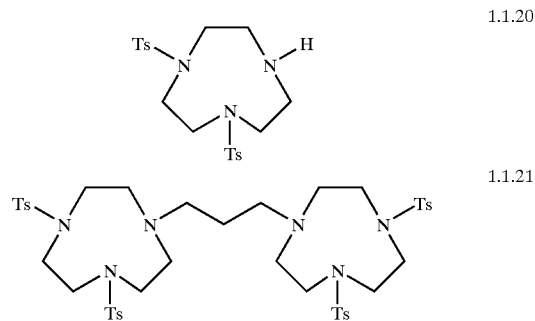

1.1.19

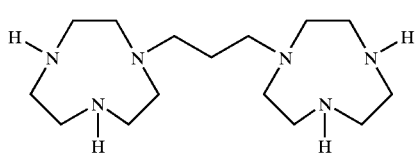

1.1.22 1,4,7,10-Tetraazabicyclo[5.5.2]tetradecane 1,4,7,10-Tetraazadodecane (1.1.4) trihydrobromide in acetonitrile with potassium carbonate was reacted with glyoxal to form 1,4,7,10-tetraazatetracyclo-[5,5,2,04,13, 010,14] tetradecane (1.1.23). Following separation the pure product was obtained by low pressure distillation. This was dissolved in acetonitrile and benzylbromide was added to form 1,7-dibenzylonium-1,4,7,10-tetraaza-tetracyclo[5,5,2, 04,13,010,14] tetradecane (1.1.24). Following recrystallization from ethanol this was reacted with sodium borohydride. HCl was added, followed by water and NaOH, and the product extracted with chloroform. Following evaporation of solvent the solids were dissolved in methanol and HBr was added to obtain 1,7-dibenzyl-1,4,7,10-tetraazabicyclo [5.5.2] tetradecane (1.1.25) as the hydrobromide salt. This was dissolved in water and reduced using $H_2$ and a Pd-C catalyst to remove the benzyl groups. Purification of the title compound was by crystallization of the hydrobromide salt. The base form was obtained by low pressure distillation following addition of base.

1.1.23

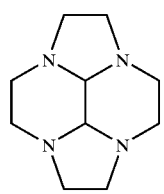

1.1.24

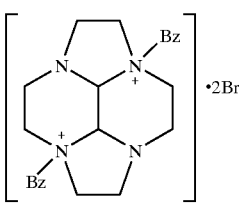

1.1.25

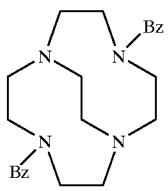

1.1.22

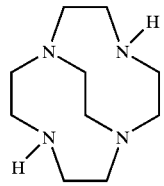

1.1.26 1,4,7,10,13-Pentaazabicyclo [8.5.2] heptadecane.

To 1,8-bis(p-toluenesulfonyloxy)-3,6-bis(p-toluenesulfonyl)-3,6-diaza-octane(1.1.27) was added 1,4,7-triazacyclononane(1.1.3) in acetonitrile with potassium bicarbonate to obtain 4,7-bis (p-toluenesulfonyl)-1,4,7,10, 13-penta-azabicyclo [8.5.2] (1.1.28) heptadecane. The title compound was purified and the p-toluenesulfonyl groups were removed by treatment in sulfuric acid. Purification was done by low pressure distillation.

1.1.27

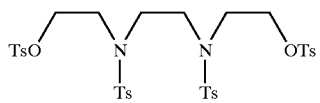

1.2.28

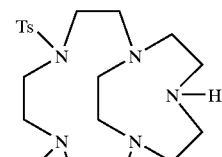

1.2.26

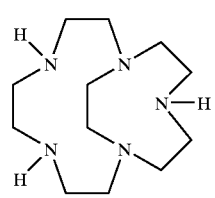

1.1.29 1,2-Bis(1,4,7-triazabicyclononane-1-yl) ethane.

A mixture of N,N'-bis(p-toluenesulfonyl)-1,4,7-triazabicyclonone hydrobromide (1.1.13.33), ethylene glycol di-p-toluenesulfonyl or dibromoethane and excess of potassium carbonate in acetonitrile was refluxed overnight. The reaction mixture was added to water and extracted with methylene chloride. The tetratosylated product (1.1.30) was purified by chromatography. It was suspended in 70% $H_2SO_4$ and heated at 150° C. for 15 hours. The reactions cooled to room temperature and then 62% HBr solution was added. The white precipitate was collected and washed with ethanol, then redissolved in water and filtered from tars. The water was made basic and the title compound (1.1.29) was extracted with chloroform.

1.1.30

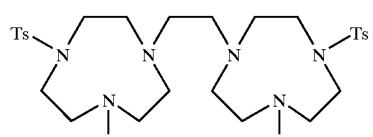

1.1.29

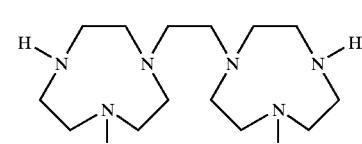

1.2 Synthesis of Alkylating Groups for Alkylation of Polyaza Bases to form Chelators Described in Example 1.3.

1.2.1 Preparation of Glycidyl Ethers

Glycidyl tosylate (R, S or d,l) (1.2.1.0) was reacted in the appropriate alcohol solvent employing catalytic amounts of conc. $H_2SO_4$ or equivalent amounts of tetrafluoroboranetherate. The 1-alkyloxy-2-hydroxy-3-p-toluenesulfonyloxypropane (1.2.1.1) product was reacted in ether with BuLi to yield the title epoxide. The following compounds were prepared in this manner.

1.2.1.0 Glycidyl tosylate (R,S or d,l; commercially available).

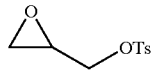

1.2.1.0

1.2.1.1 1-Alkyloxy-2-hydroxy-3-p-toluenesulfonyloxypropane.

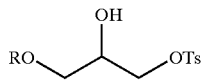

1.2.1.1

1.2.1.2 d,l-Glycidyl-isopropyl ether (commercially available).

1.2.1.2

1.2.1.3 (2R) Glycidyl-isopropyl ether.
1.2.1.4 (2S) Glycidyl-isopropyl ether.
1.2.1.5 d,l-Glycidyl-t-butyl ether.

1.2.1.5

1.2.1.6 (2R) Glycidyl-t-butyl ether.
1.2.1.7 d,l-Glycidyl allyl ether.

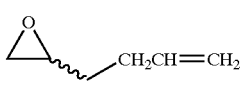

1.2.1.7

1.2.1.8 d,l-Glycidyl phenyl ether

1.2.1.8

1.2.2 Preparation of 2,2-Dialkoxymethylene Oxiranes and Spiro-Oxiranes

3-Chloro-2-chloromethyl-1-propane (1.2.2.0) was reacted with the corresponding sodium alkylate or disodium dialkylate either using the same alcohol or dialcohol as solvent or using an inert solvent. The ether product was purified by distillation or chromatography. Epoxidation was performed using meta-chloroperbenzoic acid in halogenated solvent. The following compounds were prepared in this manner.

1.2.2.0 3-Chloro-2-chloromethyl-1-propene (commercially available).

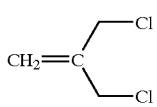

1.2.2.0

1.2.2.1 2,2-Bis-ethoxymethyl oxirane.

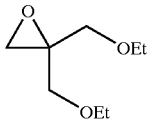

1.2.2.1

1.2.2.2 2,2-Bis-methoxymethyl oxirane.

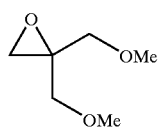

1.2.2.2

1.2.2.3 2,2-Bis-isopropyloxymethyl oxirane.

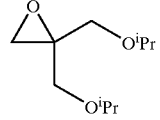

1.2.2.3

1.2.2.4 2,2-Bis-difurfuryloxymethyl oxirane.

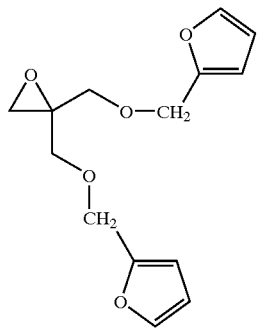

1.2.2.4

1.2.2.5 2,2-Bis(hydroxymethyl) oxirane

From 2-methylidene-1,3-dihydroxypropenediol (commercially available).

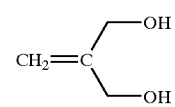

1.2.2.5

1.2.3 Preparation of Oxiranespiro-3-(1,5-Dioxacycloalkanes).

Various dry glycols in DMF were reacted with NaH and 3-chloromethyl-1-propane (1.2.2.0) was added to the resulting reaction mixture. Following completion of the reaction the solvents were removed and the product purified by low pressure distillation. The purified product in dichloroethane was reacted with m-chloroperbenzoic acid to form the corresponding epoxide. Following workup, the epoxide product was purified by distillation. The following compounds were prepared in this manner.

1.2.3.1 Oxiranespiro-3-(1,5-dioxacycloheptane).

(From ethylene glycol)

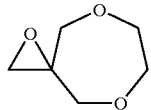
1.2.3.1

1.2.3.2 Oxiranespiro-3-(1,5-dioxa-7,7-dimethylcyclooctane).

(From 2,2-dimethyl propylene glycol)

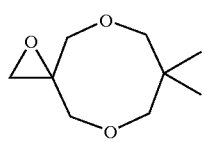
1.2.3.2

1.2.3.3 Oxiranespiro-3-(1,5-dioxa-6-methylcycloheptane).

(From 1,2-dihydroxy propane)

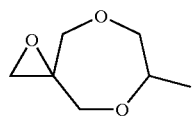
1.2.3.3

1.2.3.4 Oxiranespiro-3-(1,5-dioxa-6,6,7,7-tetramethylcycloheptane).

[From 2,3-dihydroxy-2,3-dimethyl butane (pinacol)].

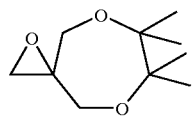
1.2.3.4

1.2.3.5 Oxiranespiro-3-(benzo[b]-1,5-dioxacycloheptane).

(From 1,2-dihydroxybenzene).

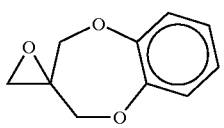
1.2.3.5

1.2.3.6 Oxiranespiro-3-(1,5-dioxacycloctane).

(From 1,3-propanediol)

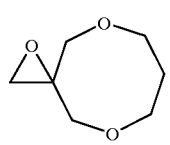
1.2.3.6

1.2.4 Preparation of Miscellaneous Epoxides
1.2.4.1 2,2-dimethyl oxirane.
(From 2-methyl-1-propene and m-chloroperbenzoic acid.

1.2.4.1

1.2.4.2 2-(Isopropyl)-2-[(1-fluoro-1-methyl)ethyl] oxirane.

Reaction between 2,4-dimethyl-3-pentanone (1.2.4.3), trimethylsilyl chloride, and base gave 2,4-dimethyl-3-trimethysilyloxy-2-pentene (1.2.4.4) which was reacted with 1-fluoropyridinium triflate (1.2.4.5) to form 2,4-dimethyl-2-fluoro-3-pentanone (1.2.4.6). This product was reacted with $(CH_3)_3S(O)^+I^-$ to form the title compound (1.2.4.2).

1.2.4.3

1.2.4.4

OSi(Me)₃

1.2.4.5

F—N⁺ Tf⁻

1.2.4.6

1.2.4.2

1.2.4.7 2,2-Bis-isopropyl oxirane.
(From 2,4-dimethylpentanone using $(CH_3)_3S(O)^+I^-$ as described in 1.2.4.2)

1.2.4.7

1.2.4.8 2-(1-Fluoroethyl)-2-(1-trimethylsilyloxyethyl) oxirane.

The title compound was obtained in several steps. DEK was O-silylated using usual procedure. The resulting product was reacted with 1-fluoropyridinium triflate (1.2.4.5) to yield 2-fluoro-3-pentanone (1.2.4.9). After bromination the 2-bromo-4-fuoro-3-pentanone (1.2.4.10) which was obtained was reacted with liquid ammonia to form 2-fluoro- 4-hydroxy-3-pentanone (1.2.4.11). The free hydroxyl group was protected with trimethylsilylchloride to form 2-fluoro-4-trimethylsilyloxo-3-pentanone (1.2.4.12). This product was reacted with trimethylsulfoxonium iodide to form the title compound (1.2.4.8).

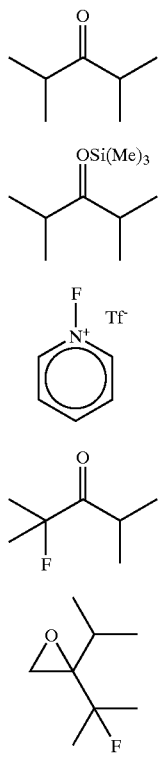

1.2.4.13 2-(1-Bromoethyl)-3-methyl oxirane.

Bromination of diethyl ketone with bromine gave 2,4-dibromo-3-pentanone (1.2.4.14). This product was reduced with BH$_3$/THF to form 3-hydroxy-2,4-dibromopentane (1.2.4.15). After treatment with base the title compound (1.2.4.13) was obtained.

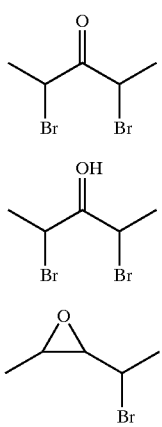

1.2.4.16 2-(1-Fluoroethyl)-3-methyl oxirane.

From reaction between diethylketone and trimethylchlorosilane to form 3-trimethylsilyloxy-2-pentene (1.2.4.17). This product was reacted with 1-fluoro-pyridinium triflate (1.2.4.5) to obtain 2-fluoro-3-pentanone (1.2.4.9). After bromination with pyridinium bromide followed by reduction using diborane 2-fluoro-4-bromopentane-3-ol (1.2.4.18) was obtained. Reaction of this product with sodium methylate yielded the title compound (1.2.4.16).

This compound was made also by reacting 2-(1-bromoethyl)-3-methyl oxirane (1.2.4.13) with HF/Py (70%) followed by treatment of the resulting 2-bromo-4-fluoropentan-3-ol (1.2.4.18) with K$_2$CO$_3$/MeOH.

1.2.4.19 2-(1-Fluoroethyl)-2-(1-methoxyethyl) oxirane.

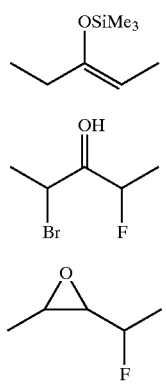

2-(1-Fluoroethyl)-3-methyl oxirane (1.2.4.16) was reacted with methanol/sulfuric acid to obtain 2-fluoro-4-methoxypentane-3-ol (1.2.4.20). This product was reacted with chromic anhydride/pyridine to form 2-fluoro-4-methoxy-pentane-3-one (1.2.4.21) which was then reacted with sodium hydride and trimethylsulfoxonium iodide to obtain the title compound (1.2.4.19).

1.2.4.22 2-(1-Methoxyethyl)-3-methyl oxirane.

Reaction of 2-(1-Bromoethyl)-3-methyl oxirane (1.2.4.13) with methanol/sulfuric acid formed 2-bromo-3-hydroxy-4-methoxypentane (1.2.4.23). This product was reacted with potassium carbonate in methanol to obtain the title compound (1.2.4.22).

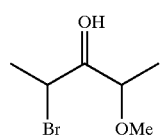

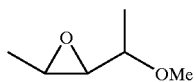
1.2.4.22

1.2.4.24 2-Ethyl-2-(1-methoxyethyl) oxirane.

Reaction between diethyl ketone and dimethyl hydrazine gave diethyl ketone-N,N-dimethylhydrazone (1.2.4.25). This product was reacted with dimethyl disulfide/LDA to obtain 2-methylthio-3-pentanone-N,N-dimethyl hydrazone (1.2.4.26). This product was reacted with mercuric chloride followed by cupric chloride to obtain 2-methoxy pentane-3-one (1.2.4.27). Reaction of the latter compound with sodium hydride/DMSO/trimethylsulfonium iodide yielded the title compound (1.2.4.24).

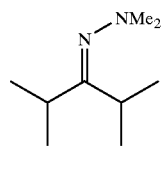
1.2.4.25

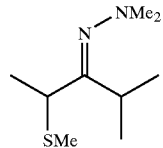
1.2.4.26

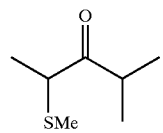
1.2.4.27

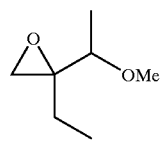
1.2.4.24

1.2.4.28 2-Ethyl-2-(1-trimethylsilyloxyethyl) oxirane.

From reaction between 2-bromo-3-pentanone (1.2.4.29) and hydrazine obtained 2-hydroxy-3-pentanone (1.2.4.30). This product was reacted with trimethylchlorosilane/triethylamine to obtain 2-trimethylsilyloxy-3-pentanone (1.2.4.31). This product was reacted with methylenetriphenyl phosphite and butyllithium to obtain 2-ethyl-3-trimethylsilyloxy-1-butene (1.2.4.32). After oxidation with meta-chloroperbenzoic acid in methylene chloride the title compound (1.2.4.28) was obtained.

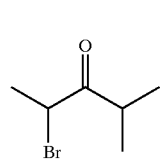
1.2.4.29

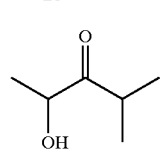
1.2.4.30

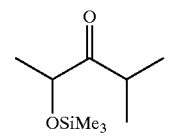
1.2.4.31

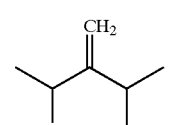
1.2.4.32

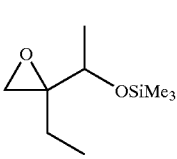
1.2.4.28

1.2.4.33 2,2-Bis(1-fluoroethyl) oxirane.

From reaction between 2-(1-Bromoethyl)-3-methyl oxirane (1.2.4.13) and HF/pyridine was obtained 2-bromo-4-fluoro-pentane-3-ol (1.2.4.18). This was reacted with potassium carbonate to obtain 2-(1-fluoroethyl)-3-methyl oxirane (1.2.4.16). This was reacted again with HF/pyridine to obtain 2,4-difluoro-pentane-3-ol (1.2.4.34). After oxidation with chromium trioxide obtained 2,4-difluoro-3-pentanone (1.2.4.35). The epoxide title compound was prepared from the ketone as described for 1.2.4.24.

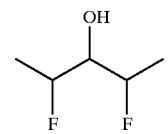
1.2.4.34

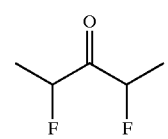
1.2.4.35

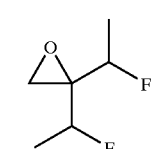
1.2.4.33

1.2.3.36 2,2-Bis-dichloromethyleneoxirane.

(From direct epoxidation of 3-chloro-2-chloromethyl-1-propene).

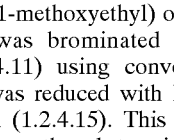
1.3.4.36

1.2.4.37 2,2-Bis(1-methoxyethyl) oxirane.

3-Pentanone was brominated to get 2,4-dibromo-3-pentanone (1.2.4.11) using conventional methods. The dibromoketone was reduced with $BH_3*THF$ to the corresponding alcohol (1.2.4.15). This compound was reacted with MeONa in methanol to yield 2-(1-bromoethyl)-3-methyl oxirane (1.2.4.13) which after reaction with MeOH/$H_2SO_4$ gave 2-bromo-3-hydroxy-4-methoxy pentane (1.2.4.38). This intermediate was reacted again with MeONa in methanol and the resulting 2-(1-methoxyethyl)-3-methyl oxirane (1.2.4.22) was reacted again with MeOH/H$_2$SO$_4$ to yield 2,4-dimethoxy-3-hydroxy pentane (1.2.4.39). After oxidation with CrO$_3$/Py in methylenechloride the resulting ketone was reacted with trimethylsulfoxonium iodide to give the title compound (1.2.4.37).

1.2.6.2 1-Bromo-2-t-butyidimethylsilyloxyethane, BrCH$_2$CH$_2$Si($^t$Bu)(CH$_3$)$_2$ (From bromoethanol and dimethyl-t-butylsilylchloride)

1.2.6.3 5-(p-Toluenesulfonyloxymethylene)-1-benzyloxy-2-pyrrolidone.

This compound was prepared in several steps. 4-pentenoic acid (1.2.6.4) was reacted with ethylchloroformate to obtain the active mixed anhydride. To a solution of the mixed anhydride in chloroform was added triethylamine and O-benzylhydroxylamine hydrochloride to obtain O-benzyl-4-pentenohydroxamic acid (1.2.6.5). The double bond was oxidized using osmium tetroxide/N-methylmorpholine oxide to give the diol (1.2.6.6). The terminal hydroxyl group was then protected with t-butyldimethylsilylchloride in the usual way to yield (1.2.6.7). The secondary hydroxyl group was tosylated using pyridine/p-toluenesulfonyl chloride. Cyclization of (1.2.6.8) to the corresponding pyrrolidone (1.2.6.9) was effected by using sodium carbonate in methanol. The protecting silyl group was removed by treatment with tetraethylammonium fluoride. The title compound (1.2.6.3) was prepared by reacting the latter compound (1.2.6.10) with pyridine/p-toluenesulfonyl chloride.

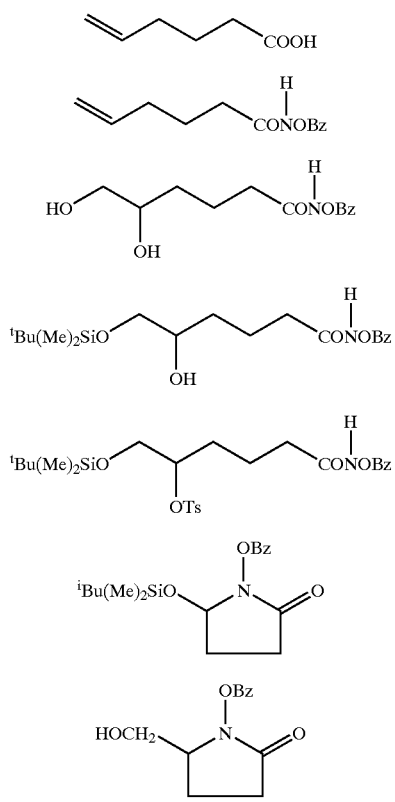

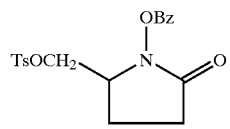

1.2.6.11 5-Bromo-1-benzyloxy-2-pyrrolidone.

This compound was prepared in several steps. Butyrolactone was reacted with PBr$_3$/Br$_2$ to obtain the dibromobutyrylbromide (1.2.6.12). This compound with O-benzylhydroxylamine yielded the protected dibromohydroxamic acid (1.2.6.13). Cyclization was effected by base to give the cyclic protected hydroxamic acid (1.2.6.11).

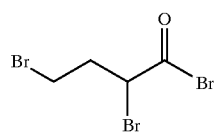

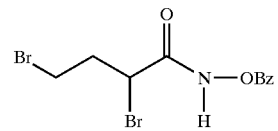

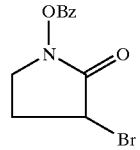

1.2.7 Preparation of N-Alkyl-O-benzylchloroacetohydroxamic Acids.

This class of compounds was prepared from chloroacetyl chloride and the suitable N-Alkylhydroxylamine followed by O-benzylation with benzyl bromide. In certain instances the O-benzyl alkylhydroxylamine was used as the starting material. O-Methyl chloroacetoxyhydroxamic acid was prepared employing O-methylhydroxylamine as starting material.

1.2.7.1 O-Benzyl-N-Methyl chloroacetohydroxamic acid, ClCH$_2$CON(Me)(OBz).

1.2.7.2 O-Benzyl-N-isopropyl-chloroacetohydroxamic acid, ClCH$_2$CON($^i$Pr)(OBz).

1.2.7.3 O-Benzyl-N-tert-butyl-chloroacetohydroxamic acid, ClCH$_2$CON($^t$Bu)(OBz).

1.2.7.4 O-Benzyl chloroacetohydroxamic acid, ClCH$_2$CONH(OBz)

1.2.7.5 O-Methyl chloroacetohydroxamic acid, ClCH$_2$CONH(OMe)

1.3 Synthesis of Chelators (Ligands)

1.3.1 Synthesis of Polyaza Ligands with Pendant Arms Containing β-Hydroxy Groups and Their Derivatives.

This family of compounds was prepared by reacting polyaza free bases with epoxides or halohydrines in water or alcohol solvents.

1.3.1.1 N,N',N"-Tris (2-hydroxy-3-isopropoxypropyl)-1,4,7-Triazacyclononane.

From 1,4,7-triazacyclononane (1.1.3) and d,l-glycidyl isopropyl ether (1.2.1.2).

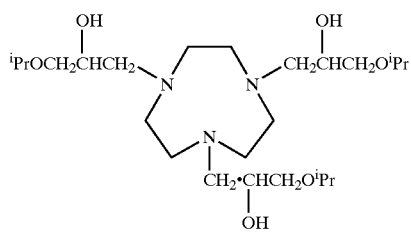

1.3.1.2 (R,R,R)N,N',N"-Tris(2-hydroxy-3-isopropoxypropyl)-1,4,7-triazacyclononane.

From 1,4,7-Triazacyclononane (1.1.3) and (2R) glycidyl isopropyl ether (1.2.1.3).

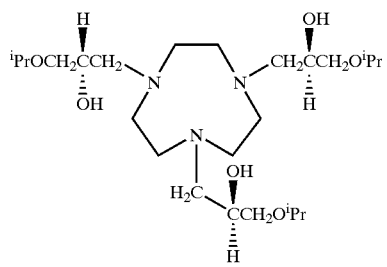

1.3.1.3 (S,S,S) N,N', N"-Tris(2-hydroxy-3-isopropoxypropyl)-1,4,7-triazacyclononane.

From 1,4,7-Triazacyclononane and (2S) glycidyl isopropyl ether (1.2.1.4).

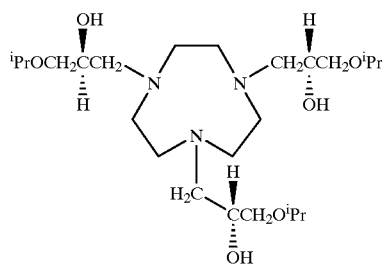

1.3.1.4 N,N',N"-Tris(2-hydroxy-3-t-butoxypropyl)-1,4,7-triazacyclononane.

From 1,4,7-Triazacyclononane (1.13) and (d,l) glycidyl-t-Butyl ether (1.2.1.5).

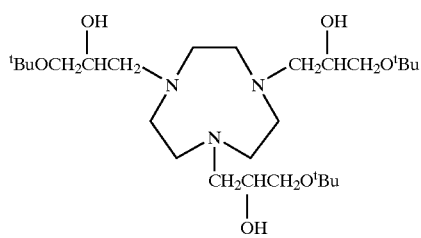

1.3.1.5 (R,R,R)N,N',N"-Tris(2-hydroxy-3-t-butoxypropyl)-1,4,7-triazacyclononane.

From 1,4,7-triazacyclononane (1.1.3) and (R) glycidyl t-butyl ether (1.2.1.6).

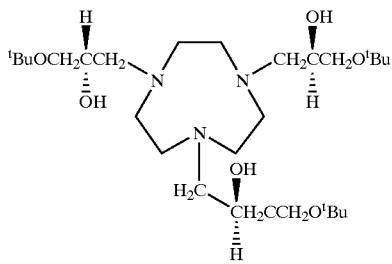

1.3.1.6 N,N',N"-Tris(2-hydroxy-3 methoxypropyl)-1,4,7-triazacyclononane

From 1,4,7-triazacyclononane (1.1.3) and (d,l) glycidyl methyl ether (commercially available).

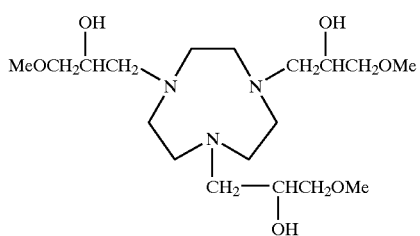

1.3.1.7 N,N',N"-Tris(2,3-dihydroxypropyl)-1,4,7-triazacyclononane.

From 1,4,7-triazacyclononane (1.1.3) and 1-bromo-2,3-dihydroxypropane (commercially available) and excess of potassium carbonate or 1-chloro-2,3-dihydroxypropane (commercially available) and base.

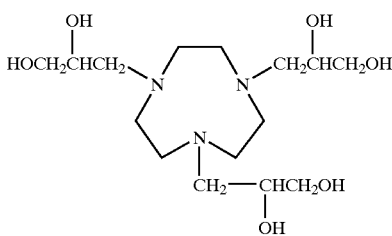

1.3.1.8 N,N',N"-Tris(1-methoxy-2-hydroxy-2-methylpropyl)-1,4,7-triazacyclononane.

From 1,4,7-triazacyclononane (1.1.3) and (d,l) 3,3-dimethyl-2-methoxy oxirane (1-methoxy-2-methylpropylene, commercially available).

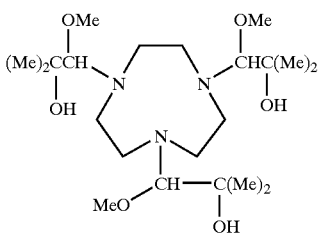

1.3.1.9 N,N',N"-Tris(2-hydroxy-3-allyloxypropyl)-1,4,7-triazacyclononane.

From 1,4,7-triazacyclononane (1.1.3) and (d,l) glycidyl allyl ether (1.2.1.7).

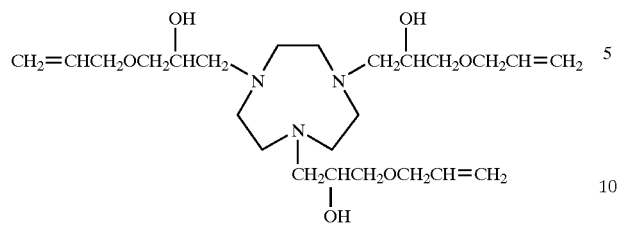

1.3.1.10 N,N',N''-Tris(2-hydroxy-3-phenoxypropyl)-1,4,7-triazacyclononane.

From 1,4,7-triazacyclononane (1.1.3) and (d,l) glycidyl phenyl ether (1.2.1.8).

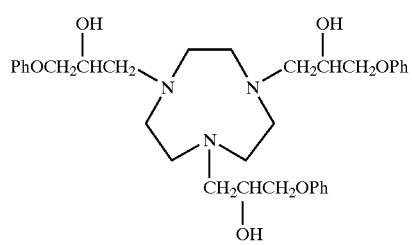

1.3.1.11 N,N',N''-Tris(2-hydroxy-2,2-diethoxymethylene)ethyl-1,4,7-triazacyclononane.

From 1,4,7-triazacyclononane (1.1.3) and 2,2-bis-ethoxymethyl oxirane(1.2.2.1).

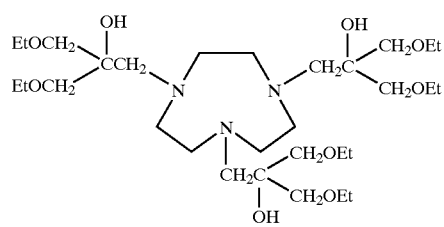

1.3.1.12 N,N', N''-Tris(2-hydroxy-2,2-dimethoxymethyl)ethyl-1,4,7-triazacyclononane.

From 1,4,7-triazacyclononane (1.1.3) and 2,2-bis-methoxyoxymethyl oxirane (1.2.2.2).

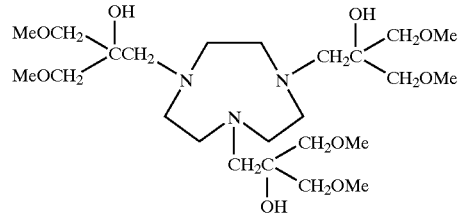

1.3.1.13 N,N',N''-Tri(2-hydroxy-(2,2-diisopropyloxymethyl)ethyl-1,4,7-triazacyclononane.

From 1,4,7-triazacyclononane (1.1.3) and 2,2-Bis-Isopropoxymethyl oxirane (1.2.2.3).

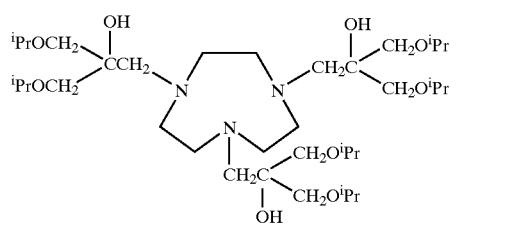

1.3.1.14 N,N',N''-Tris[2-hydroxy-bis(2-furfuryloxymethyl)ethyl]-1,4,7-triazacyclononane.

From 1,4,7-triazacyclononane (1.1.3) and 2,2-bis(furfuryloxymethyl) oxirane (1.2.2.4).

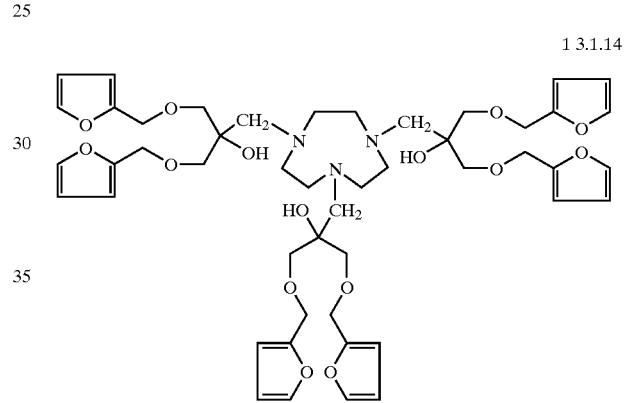

1.3.1.15 N,N',N''-Tris(3-hydroxy-1,5-dioxacycloheptyl-3-methyl)-1,4,7-triazacyclononane.

From 1,4,7-triazacyclononane (1.1.3) and oxiranespiro-3-(1,5-dioxacycloheptane) (1.2.3.1).

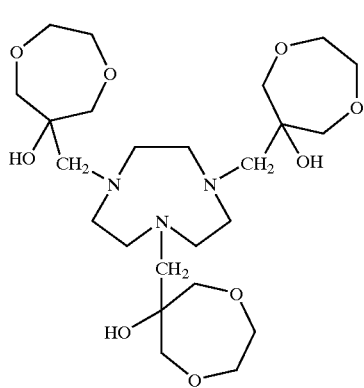

1.3.1.16 N,N', N"-Tris[(3-Hydroxy-7,7-dimethyl-1,5-dioxacyclooct-3-yl)-methyl]-1,4,7-triazacyclononane.

From 1,4,7-triazacyclononane (1.1.3) and oxiranespiro-3-(1,5-dioxa-7,7-dimethylcyclooctane) (1.2.3.2).

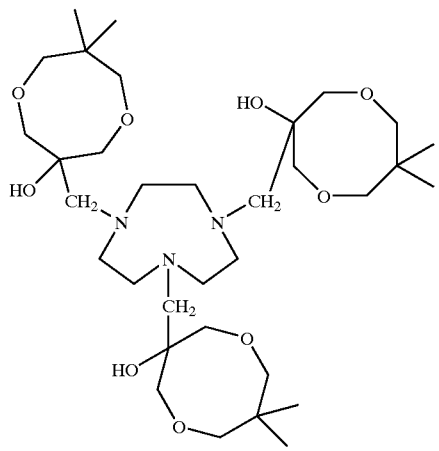

1.3.1.16

1.3.1.17 N,N', N"-Tris[(3-hydroxy-7-methyl-1,5-dioxacyclohept-3-yl)methyl]-1,4,7-triazacyclononane.

From 1,4,7-triazacyclononane (1.1.3) and oxiranespiro-3-(1,5-dioxa-6-methylcycloheptane(1.2.3.3).

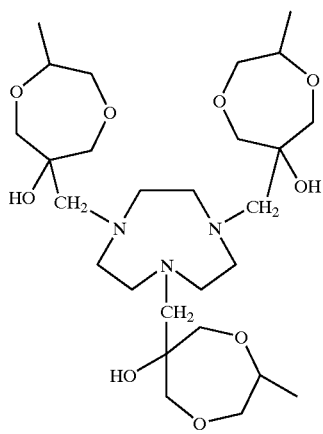

1.3.1.17

1.3.1.18 N,N',N"-Tris[(3-hydroxy-6,6,7,7-tetramethyl-1,5-dioxacyclohept-3-yl)methyl]-1,4,7-triazacyclononane.

From 1,4,7-triazacyclononane (1.1.3) and oxiranespiro-3-(1,5-dioxa-6,6,7,7-tetramethylcycloheptane) (1.2.3.4).

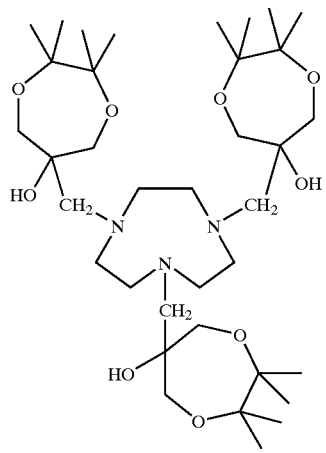

1.3.1.18

1.3.1.19 N,N',N"-Tris[(3-hydroxy-benzo[b]-1,5-dioxacycloheptyl)methyl]1,4,7-triazacyclononane.

From 1,4,7-triazacyclononane (1.1.3) and oxiranespiro-3-(benzo[b]-1,5-dioxacycloheptane) (1.2.3.5).

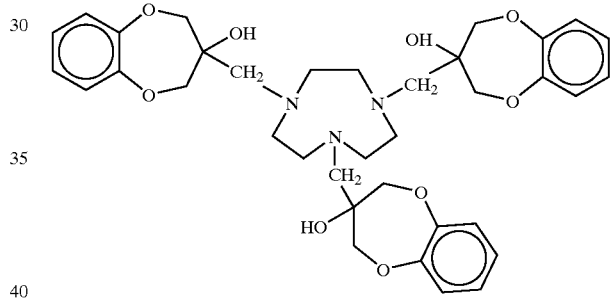

1.3.1.19

1.3.1.20 N,N', N"-Tris[(3-hydroxy-1,5-dioxacyclooctane-3-yl)methyl]-1,4,7-triazacyclononane.

From 1,4,7-triazacyclononane (1.1.3) and oxiranespiro-3-(1,5-dioxacyclooctane) (1.2.3.6).

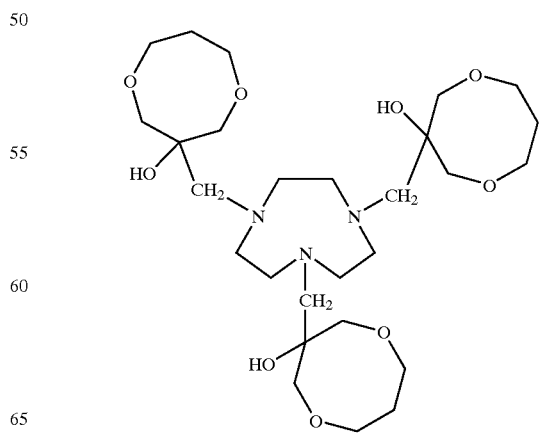

1.3.1.1.20

1.3.1.21 N,N',N''-Tris(2-hydroxy-2-methylpropyl)-1,4,7-triazacyclononane.

From 1,4,7-triazacyclononane (1.1.3) and 2,2-dimethyl oxirane (1.2.4.1)

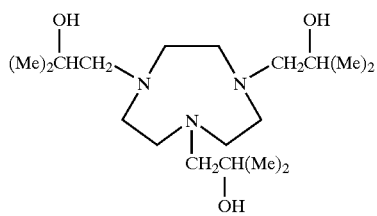

1.3.1.22 N,N',N''-Tris[(4-fluoro-2-hydroxy-3-i-propyl-4-methyl) pentyl]-1,4,7-triazacyclononane.

From 1,4,7-triazacyclononane (1.1.3) and 2-isopropyl-2-(1-fluoro-1-methylethyl) oxirane (1.2.4.2).

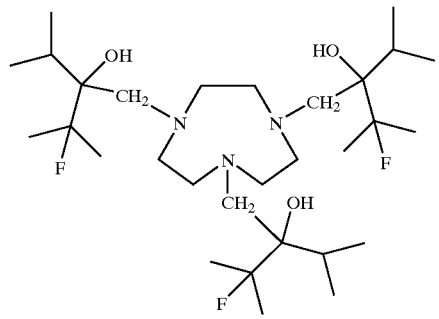

1.3.1.23 N,N',N''-Tris-[2-hydroxy-3-(1-fluoroethyl)-4-hydroxypentyl]-1,4,7-triazacyclononane.

From 1,4,7-triazacyclononane (1.1.3) and 2-(1-trimethylsilyloxyethyl)-2-(1-fluoroethyl) oxirane (1.2.4.8).

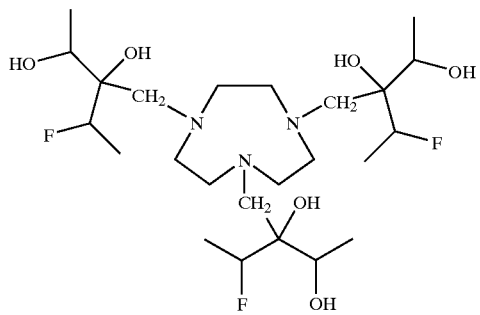

1.3.1.24 N,N',N''-Tris[2-hydroxy-2-(1-fluoroethyl)-2-(1-methoxyethyl)ethyl]-1,4,7-triazacyclononane.

From 1,4,7-triazacyclononane (1.1.3) and 2-(1-Fluoroethyl)-2-(1-methoxyethyl) oxirane (1.2.4.19).

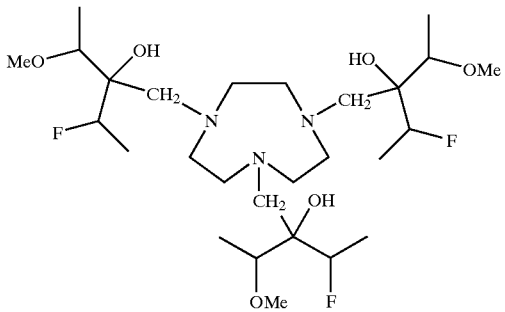

1.3.1.25 N,N',N''-Tris(2-hydroxy-2-ethyl-3-methoxy butyl)-1,4,7-triazacyclononane.

From 1,4,7-triazacyclononane (1.1.3) and 2-ethyl-2-(1-methoxyethyl) oxirane (1.2.4.24).

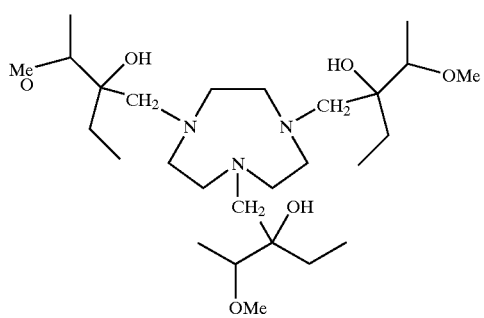

1.3.1.26 N,N',N''-Tris(2,3-dihydroxy-2-ethyl)butyl]-1,4,7-Triazacyclononane.

From 1,4,7-triazacyclononane (1.1.3) and 2-ethyl-2-(1-trimethylsilyloxyethyl) oxirane (1.2.4.28).

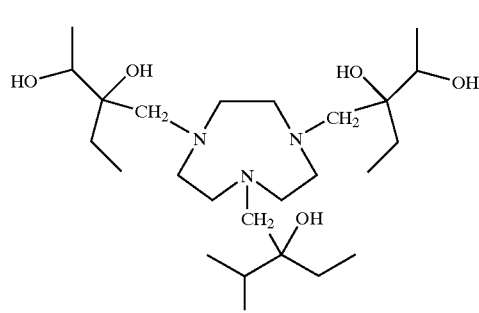

1.3.1.27 N,N',N''-Tris[2-hydroxy-2,2-bis(1-fluoro ethyl) ethyl]-1,4,7-triazacyclononane.

From 1,4,7-triazacylononane (1.1.3) and 2,2-bis(1-fluoroethyl) oxirane (1.2.4.33).

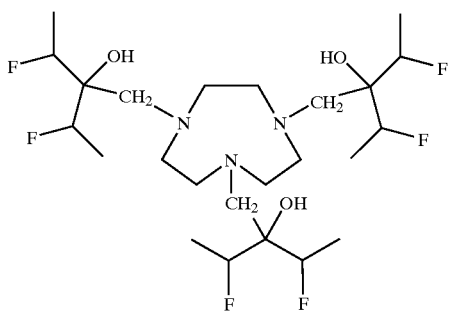

1.3.1.28 N,N',N"-Tris[2-hydroxy-2,2-bis(1-methoxyethyl)ethyl]-1,4,7-triazacyclononane.

From 1,4,7-triazacyclononane (1.1.3) and 2,2-(1-methoxyethyl) oxirane (1.2.4.37).

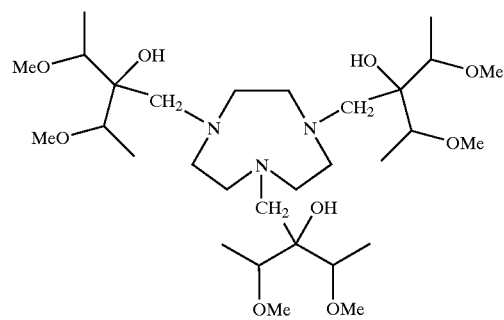

1.3.1.29 N,N',N"-Tris[(3,3-dimethyl-2-hydroxy)butyl]-1,4,7-triazacyclononane.

From 1,4,7-Triazacyclononane (1.1.3), 1-Bromo-2-hydroxy-3,3-dimethylbutane (1.2.6.1) and sodium carbonate.

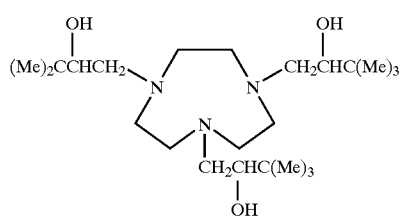

1.3.1.30 N,N',N"-Tris(2-hydroxypropyl)-1,4,7-triazacyclononane.

From 1,4,7-triazacyclononane (1.1.3) and propylene oxide.

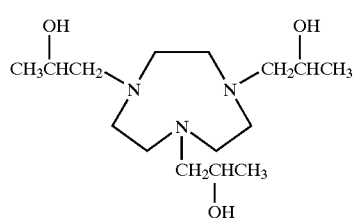

1.3.1.31 N,N',N"-Tris(2,2-dimethoxyethanyl)-1,4,7-triazacyclononane.

From 1,4,7-triazacyclononane (1.1.3), 1-chloro-2,2-dimethoxyethane (commercially available) and sodium carbonate.

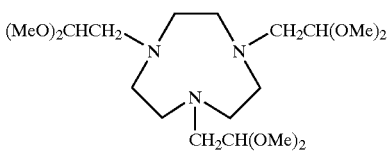

1.3.1.32 N,N',N"-Tris(2-hydroxycyclopentan-1-yl)-1,4,7-triazacyclononane.

From 1,4,7-triazacyclononane (1.1.3), 1,2-epoxycyclopentane (commercially available) and sodium carbonate.

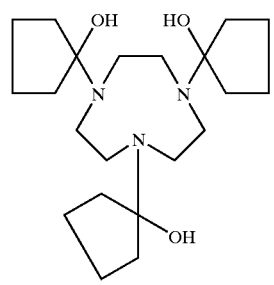

1.3.1.33 N,N',N"-Tris(2-hydroxycyclohexane-1-yl)-1,4,7-triazacyclononane.

From 1,4,7-triazacyclononane (1.1.3), 1,2-epoxycyclohexane (commercially available) and sodium carbonate.

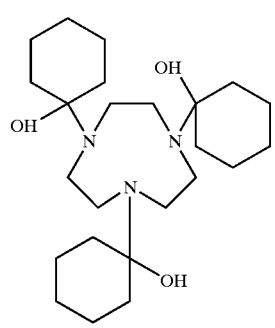

1.3.1.34 N,N',N"-Triallyl-1,4,7-Triazacyclononane.

From 1,4,7-triazacyclononane (1.1.3), sodium hydride and allyl bromide.

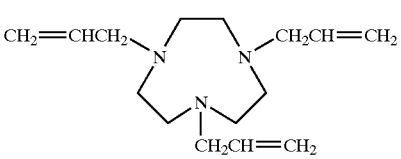

1.3.1.35 N,N',N"-Tris[(3-chloro-2-hydroxy)propyl]-1,4,7-Triazacyclononane.

From N,N',N"-triallyl-1,4,7-triazacyclononane(1.3.1.34) and aqueous chlorine.

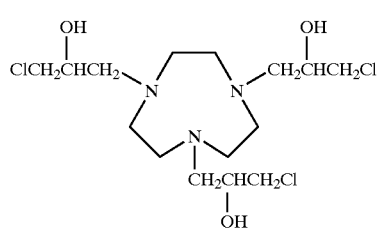

1.3.1.35

1.3.1.36 1,2-Bis-(N,N'-di-2-hydroxyethyl-1,4,7-triazacyclononane-1-yl) ethane.

From 1,2-bis-(1,4,7-triazacyclononane-1-yl) ethane polyhydrobromide and ethylene oxide.

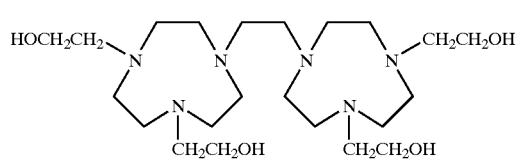

1.3.1.36

1.3.1.37 N,N',N'',N'''-Tetrakis-(2-hydroxyethyl)-1,4,7,10-tetraazacyclododecane.

From 1,4,7,10-Tetraazacyclododecane (1.1.4) and bromoethanol.

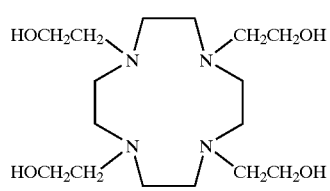

1.3.1.37

1.3.1.38 N,N',N'',N'''-Tetrakis(2,3-dihydroxypropyl)-1,4,7,10-tetraazacyclotetradecane.

From 1,4,7,10-tetraazacyclotetradecane (1.1.4), 1-chloro-2,3-propanediol (commercially available) and base.

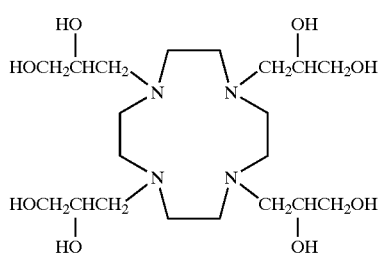

1.3.1.38

1.3.1.39 4,10-Bis(2-Hydroxypropyl)-1,4,7,10-tetraazabicyclo [5.5.2] tetradecane.

From 1,4,7,10-tetraazabicyclo[5.5.2]tetradecane (1.1.4) and propylene oxide.

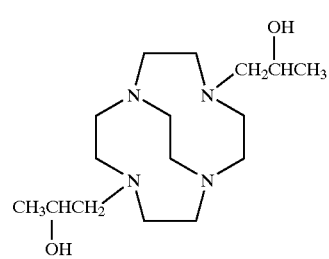

1.3.1.39

1.3.1.40 4,10-Bis-(2-hydroxyethyl)-1,4,7,10-tetraazabicyclo [5.5.2]tetradecane.

From 4,10-Bis(dimethoxycarbonylmethyl)-1,4,7,10-tetraazabicyclo[5.5.2] tetradecane (1.3.6.8) and lithium aluminum hydride.

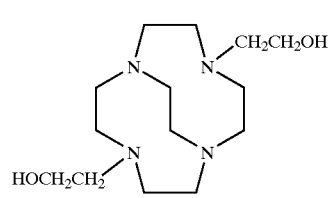

1.3.1.40

1.3.1.41 4,10-Bis[(2-Hydroxy-2-phenyl)ethyl]-1,4,7,10-tetraazabicyclo[5.5.2]tetradecane.

From 1,4,7,10-Tetraazabicyclo[5.5.2]tetradecane (1.1.4) and styrene oxide.

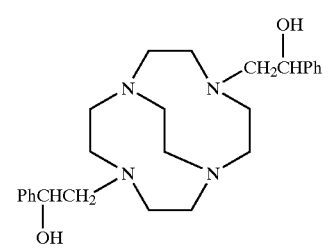

1.3.1.41

1.3.1.42 4,10-Bis-(2,3-dihydroxypropyl)-1,4,7,10-tetraazabicyclo [5.5.2] tetradecane.

From 1,4,7,10-tetraazabicyclo[5.5.2]tetradecane (1.1.4) and glycidol.

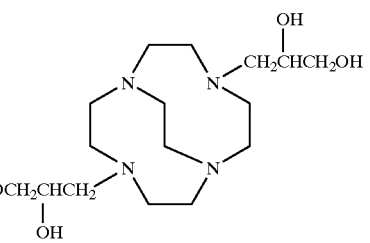

1.3.1.42

1.3.1.43 N,N',N'',N'''-Tetrakis-(2,3-dihydroxypropyl)-1,4,8,11-tetraazacyclohexadecane.

From cyclam (1.1.5) and glycidol.

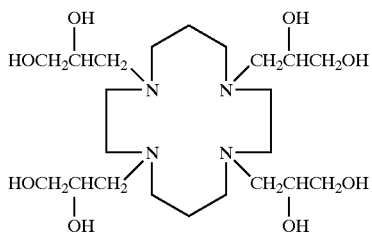

1.3.1.44 cis, trans N,N,N',N'-Tetrakis(2,3-dihydroxypropyl)-1,2-diamino-cyclohexane.

From cis,trans 1,2-diaminocyclohexane (commercially available) and glycidol.

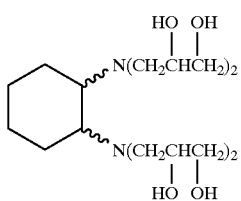

1.3.1.45 trans N,N,N',N'-Tetrakis(2,3-dihydroxypropyl)-1,2-diamino-cyclohexane.

From trans-1,2-diaminocyclohexane (commercially available) and glycidol.

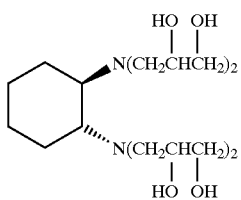

1.3.1.46 N,N,N',N'-Tetrakis(2,3-dihydroxypropyl)-ethylenediamine.

From ethylenediamine (1.1.0) and glycidol.

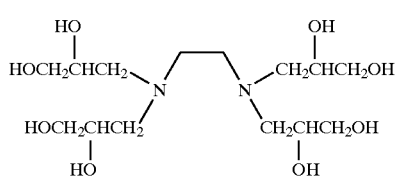

1.3.1.47 N,N,N',N'',N'''-Pentakis(2,3-dihydroxypropyl)-diethylenetriamine.

From diethylenetriamine (1.1.1), 1-chloro-2,3-propanediol and base.

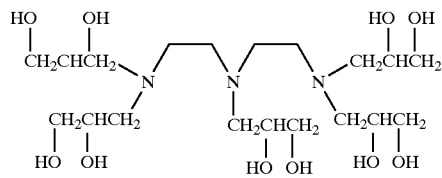

1.3.1.48 N,N,N',N'',N''', N'''-Hexaakis(2,3-dihydroxypropyl) triethylenetetramine.

From triethylenetetramine (1.1.2) and glycidol.

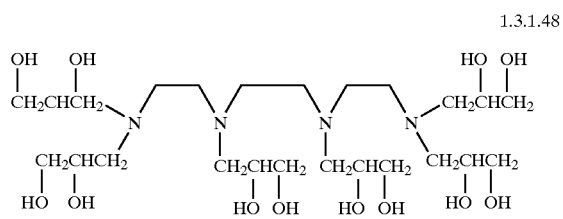

1.3.1.49 N,N,N',N'-Tetrakis(2,3-dihydroxypropyl)-1,2-diamino-2-methylpropane.

From 1,2-diaminomethylpropane and glycidol.

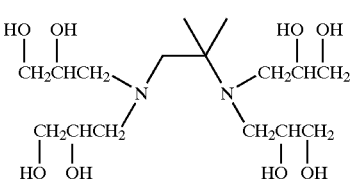

1.3.1.50 N,N,N',N'-Tetrakis(2,3-dihydroxypropyl)-1,2-diaminopropane.

From 1,2-diaminopropane and glycidol.

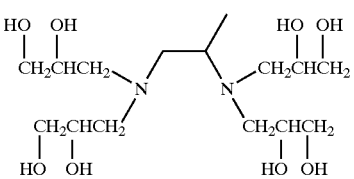

1.3.1.51 N,N',N''-Tris(2,3-diacetoxypropyl)-1,4,7-triazacyclononane.

From 1.3.1.7 and Py/Ac$_2$O.

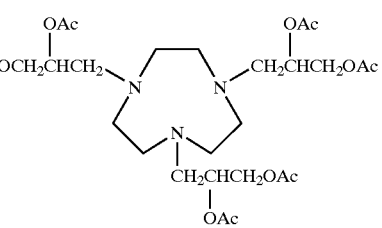

1.3.1.52 N,N',N''-tris(Dimethyl-2,3-isopropylidene propyl)-1,4,7-triazacyclononane.

From 1.3.1.7 and 2,2-dimethoxypropane/p-toluenesulfonic acid.

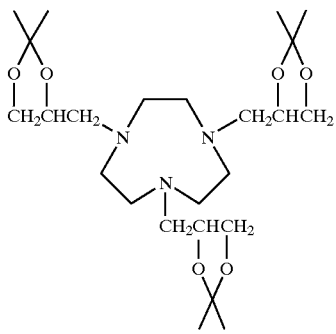

1.3.1.53 4,10-(2-Diacetoxyoxypropyl)-1,4,7,10-tetraazabicyclo [5.5.2] tetradecane.
From 1.3.1.39 and Py/Ac$_2$O.

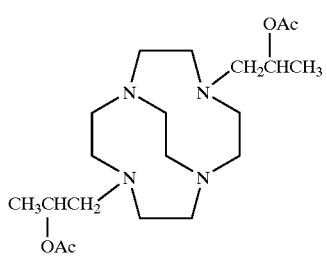

1.3.1.54 N,N',N''-Tris[(2,4-dihydroxy-3-isopropyl-4-methyl)pentyl]-1,4,7-triazacyclononane.
From 1,4,7-triazacyclononane (1.1.3) and 2,2-bis(hydroxymethyl) oxirane.

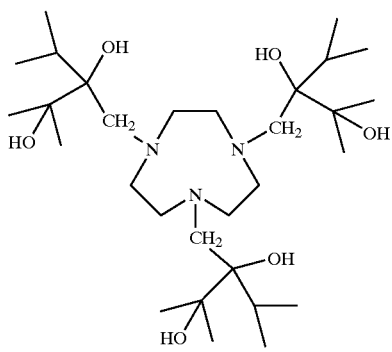

1.3.1.55 N,N',N''-Tris-[2-hydroxy-(2,2-dihydroxymethyl)ethyl]-1,4,7-triazacyclononane.
From 1,4,7-triazacyclononane (1.1.3) and 2,2-bis(hydroxymethyl) oxirane

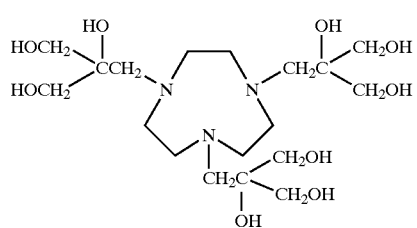

1.3.2 Synthesis of Polyaza Ligands With Alkylphosphonate Mono- and Di-Esters Pendant Arms.

1.3.2.1 Preparation

Chelators having three identical methylene phosphonate diester arms were prepared by reacting the trihydrobromide polyaza bases with formaldehyde and dialkylphosphite. The hexa-ester was hydrolized to the tri-ester by heating with NaOH dissolved in the appropriate alcohol (the same R group as in the dialkylphosphite). In some cases products were obtained by reacting the amine base with haloalkylphosphonates or epoxyphosphonates.

1.3.2.1 N,N',N''-Tris(dibutylphosphorylmethyl)-1,4,7-triazacyclononane.
From 1,4,7-triazacyclononane (1.1.3) trihydrobromide, formaldehyde solution and di-n-butyl phosphite (1.2.5.1).

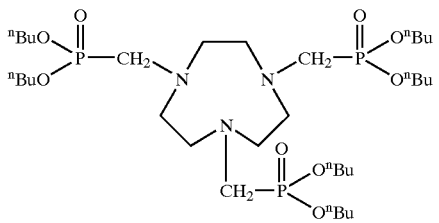

1.3.2.2 N,N',N''-Tris(dihydroxyphosphorylmethyl mono butyl ester)-1,4,7-triazacyclononane.
From N,N',N''-tris(dibutylphosphorylmethyl)-1,4,7-triazacyclononane (1.3.2.1) and KOH/butanol.

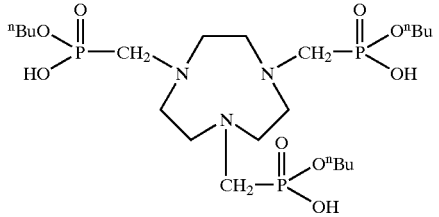

1.3.2.3 N,N',N''-Tris(diethylphosphorylmethyl)-1,4,7-triazacyclononane.
From 1,4,7-triazacyclononane (1.1.3) trihydrobromide, formaldehyde solution and diethyl phosphite (commercially available).

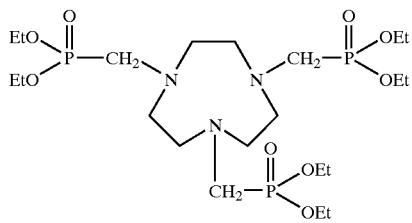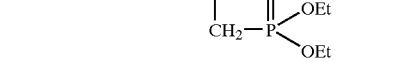

1.3.2.4 N,N',N''-Tris(dihydroxyphosphorylmethyl monoethyl ester)-1,4,7-triazacyclononane.
From N,N',N''-tris(diethylphosphorylmethyl)-1,4,7-triazacyclononane (1.3.2.3) and NaOH/EtOH.

1.3.2.4

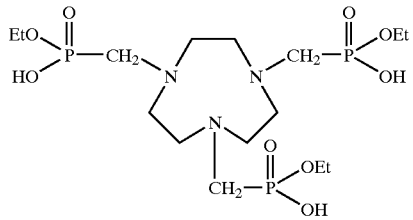

1.3.2.5 N,N',N''-Tris(dioctylphosphorylmethyl)-1,4,7-triazacyclononane.

From 1,4,7-triazacyclononane (1.1.3), formaldehyde and dioctylphosphite (1.2.5.2).

1.3.2.5

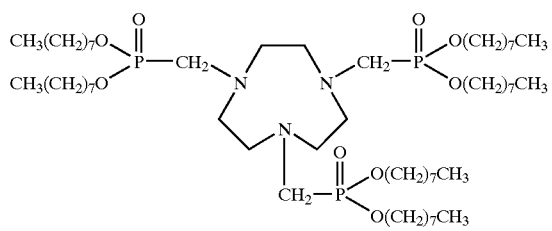

1.3.2.6 N,N',N''-Tris(dihydroxyphosphorylmethyl monooctyl ester)-1,4,7-triazacyclononane.

From 1.3.2.5 and NaOH in octyl alcohol.

1.3.2.6

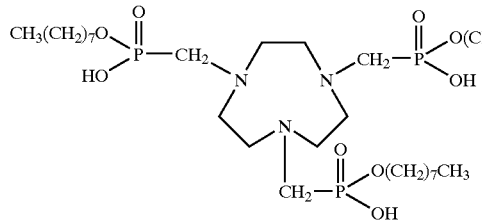

1.3.2.7 N,N',N''-Tris(diisobutylphosphorylmethyl)-1,4,7-triazacyclononane.

From 1,4,7-triazacyclononane (1.1.3), formaldehyde and diisobutylphosphite (1.2.5.3).

1.3.2.7

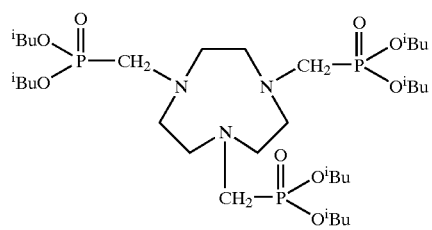

1.3.2.8 N,N',N''-Tris(dihydroxyphosphorylmethyl monoisobutyl ester)-1,4,7-triazacyclononane.

From 1.3.2.7 and NaOH in isobutyl alcohol.

1.3.2.8

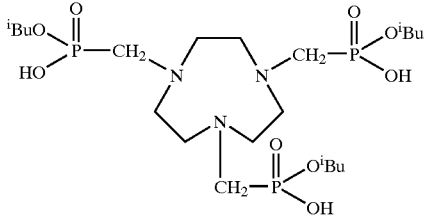

1.3.2.9 N,N',N''-Tris(dibenzylphosphorylmethyl)-1,4,7-triazacyclononane.

From 1,4,7-triazacyclononane (1.1.3), formaldehyde and dibenzylphosphite (1.2.5.4).

1.3.2.9

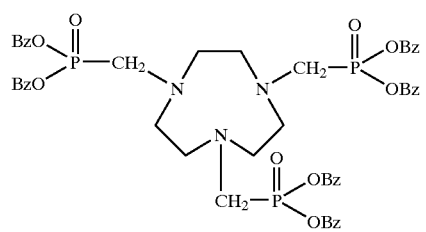

1.3.2.10 N,N',N''-Tris(diethylphosphorylethyl)-1,4,7-triazacyclononane.

From 1,4,7-triazacyclononane (1.1.3) trihydrobromide, potassium carbonate and diethyl(2-bromoethyl)phosphonate (1.2.5.5).

1.3.2.10

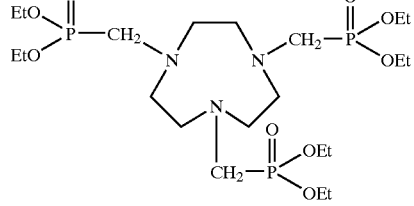

1.3.2.11 N,N',N'',N'''-Tetrakis(diethylphosphorylmethyl)-1,4,7,10-tetraazacyclodecane.

From 1,4,7,10-tetraazacyclodecane (1.1.4) trihydrobromide, formaldehyde and diethylphosphite (commercially available).

1.3.2.11

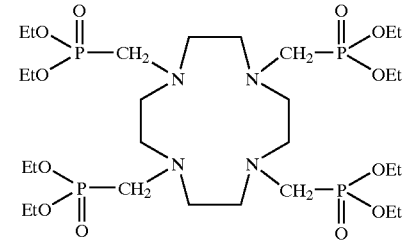

1.3.2.12 N,N',N'',N'''-Tetrakis(diethylphosphorylethyl)-1,4,7,10-tetraazacyclododecane.

From 1,4,7,10-tetraazacyclododecane (1.1.4) trihydrobromide, potassium carbonate and diethyl(2-bromoethyl)phosphonate (1.2.5.5).

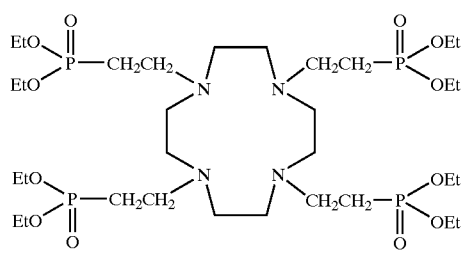

1.3.2.12

1.3.2.13 4,10-Bis(diethylyphosphorylethyl)-1,4,7,10-tetraazabicyclo [5.5.2] tetradecane.

From 1,4,7,10-tetraazabicyclo[5.5.2]tetradecane (1.1.20) dihydrobromide, potassium carbonate and diethyl(2-bromoethyl)phosphonate (1.2.5.5).

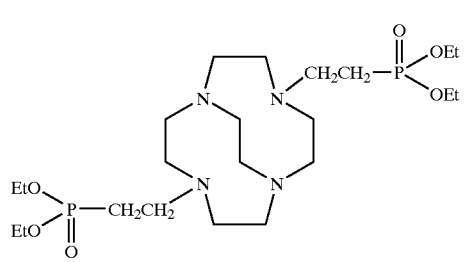

1.3.2.13

1.3.2.14 4,10-Bis(diethylphosphoryl methyl)-1,4,7,10-tetraazabicyclo [5.5.2] tetradecane.

From 1,4,7,10-tetraazabicyclo[5.5.2]tetradecane (1.1.20) trihydrobromide, formaldehyde and diethylphosphite (commercially available).

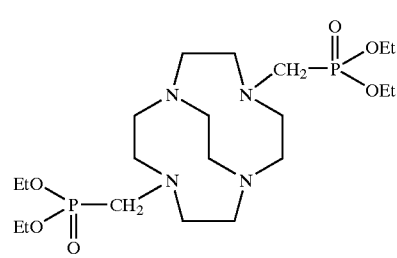

1.3.2.14

1.3.2.15 N,N',N''-Tris(diethylphosphorylmethyl)-1,4,7,10,13-pentaazabicyclo [8.5.2]heptadecane.

From 1,4,7,10,13-pentaazabicyclo[8.5.2]heptadecane (1.1.25), formaldehyde and diethylphosphite (commercially available).

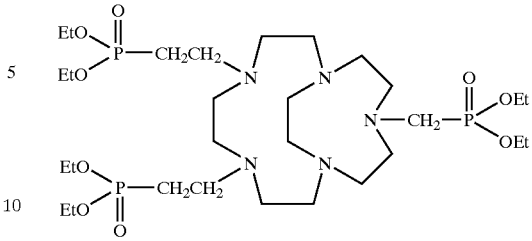

1.3.2.15

1.3.3 Synthesis of Polyaza Ligands with Identical Alkylphosphonic Acid Pendant Arms.

These compounds were prepared by either hydrolizing the ester groups of the compounds described under 1.3.2, or from the polyaza base, formaldehyde and phosphorous acid.

1.3.3.1 1,2-Bis(N,N'-bis(dihydroxyphosphrylmethyl)-1,4,7-triazacyclonan-1-yl) ethane.

From 1,2-bis-(1,4,7-triazacyclononan-1-yl)ethane (1.1.28), formaldehyde and phosphorous acid.

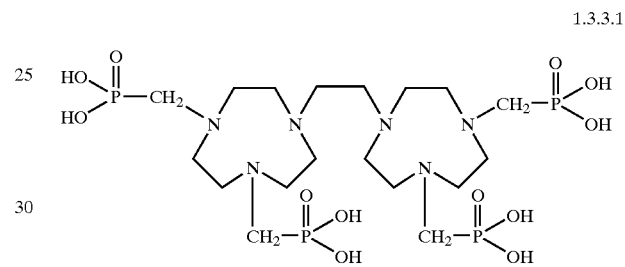

1.3.3.1

1.3.3.2 1,2-Bis(N,N'-bis(dihydroxyphosphorylmethyl)-1,4,7-triazacyclononan-1-yl)propane.

From 1,2-bis-(1,4,7-triazacyclononan-1-yl)propane (1.1.19), formaldehyde and phosphorous acid.

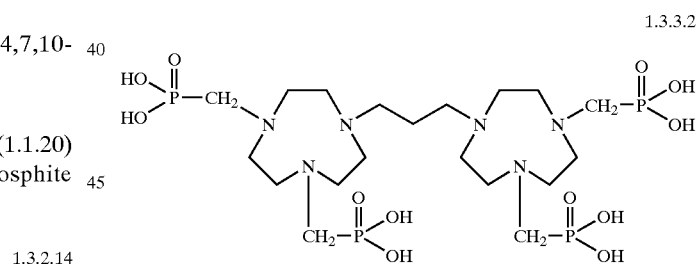

1.3.3.2

1.3.3.3 4,10-Bis(dihydroxyphosphorylmethyl)-1,4,7,10-tetraazabicyclo[5.5.2]tetradecane.

From 1,4,7,10-tetraazabicyclo[5.5.2]tetradecane (1.1.20) trihydrobromide, formaldehyde and phosphorous acid.

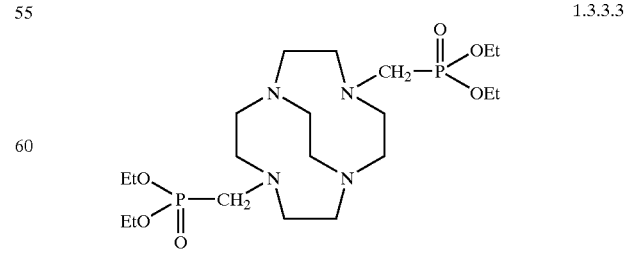

1.3.3.3

1.3.3.4 4,7,13-Tris(dihydroxyphosphorylmethyl)-1,4,7,10,13-pentaazabicyclo[8.5.2]heptadecane.

From hydrolysis of 1,4,7,13-tris(diethylphosphorylmethyl)-1,4,7,10,13-pentaazabicyclo[8.5.2]heptadecane (1.3.2.15) by HCl.

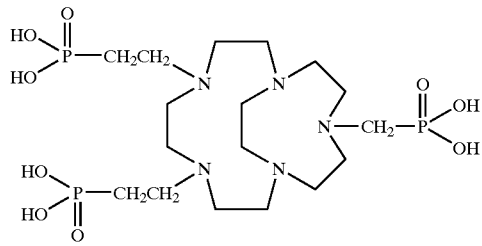

1.3.3.4

The following compounds were prepared from the corresponding diesters by hydrolysis with HCl:

1.3.3.5 N,N',N''-Tris(dihydroxyphosphorylethyl)-1,4,7-triazacyclononane.

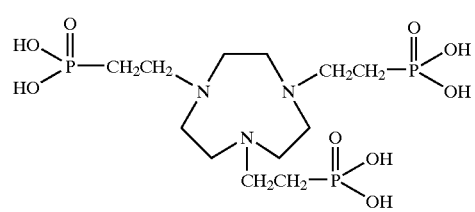

1.3.3.5

1.3.3.6 N,N',N'',N'''-Tetrakis(dihydroxyphosphorylethyl)-1,4,7,10-tetraazacyclododecane.

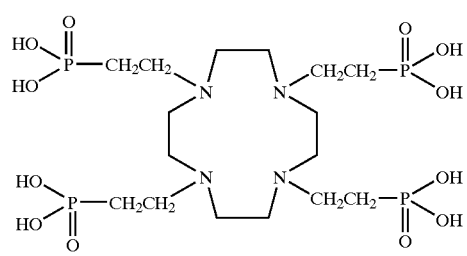

1.3.3.6

1.3.3.7 4,10-Bis(dihydroxyphosphorylethyl)-1,4,7,10-tetraazabicyclo[5.5.2] tetradecane.

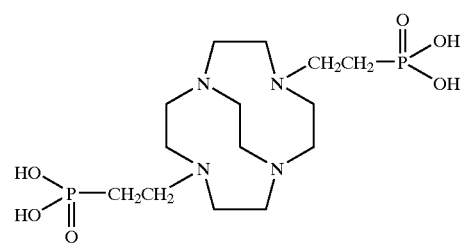

1.3.3.7

1.3.4 Synthesis of Polyaza Ligands with Pendant Arms Containing Phosphonate Esters and Acids with Alpha Substituent Groups.

Alkyl or aryl groups a to the phosphonate moiety were prepared by alkylation of the corresponding ligand in the form of its dialkylphosphonate.

1.3.4.1 N,N',N''-Tris[α-dihydroxyphosporyl-α-benzyl)methyl]-1,4,7-triazacyclononane.

From N,N',N''-Tris[(α-diethylphosporyl-α-benzyl)methyl]-1,4,7-triazacyclononane (U.S. Pat. No. 5,380,515) and trimethylsilyl iodide.

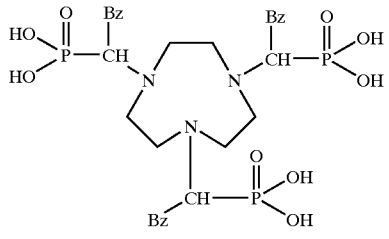

1.3.4.1

1.3.4.2 N,N',N''-Tris{[(diethylphosphoryl)-α-hydroxy]ethyl}-1,4,7-triazacyclononane.

From 1,4,7-triazacyclononane (1.1.3) and 2-diethylphosphoryl oxirane (1.2.5.7).

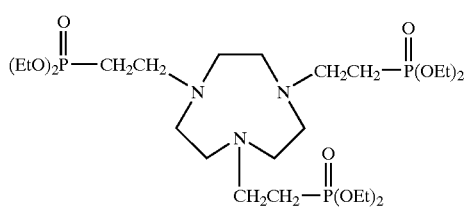

1.3.4.2

1.3.4.3 N,N',N''-Tris[dihydroxyphosphoryl-α-hydroxy)ethyl]-1,4,7-triazacyclononane.

From 1.3.4.2 and HCl.

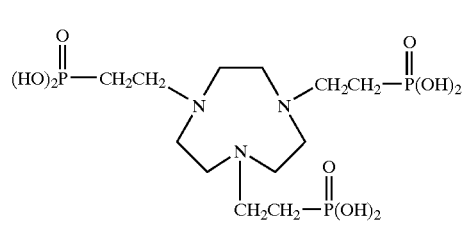

1.3.4.3

1.3.5 Synthesis of Polyaza Ligands with Pendant Arms Containing Hydroxamate Groups.

These compounds were prepared by reacting 1,4,7-tetraazacyclononane (1.1.3) trihydrobromide with a N-alkyl-O-benzyl chloroacetohydroxamic acid in the presence of a base. The free hydroxamic acid was obtained by removing the benzyl protecting group by hydrogenolysis.

1.3.5.1 N,N',N''-Tris[(N-methyl-N-benzyloxycarbamoyl)methyl]1,4,7-triazacyclononane.

From 1,4,7-triazacyclononane, sodium carbonate and O-benzyl-N-methyl chloroacetohydroxamate (1.2.7.1).

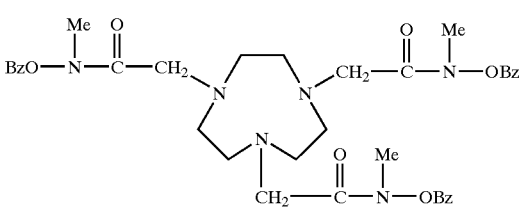

1.3.5.1

1.3.5.2 N,N',N''-Tris[(N-methyl-N-hydroxycarbamoyl)methyl]-1,4,7-triazacyclononane.

From N,N',N"-tris[(N-methyl-N-benzyloxycarbamoyl)methyl]-1,4,7-triazacyclononane (1.3.5.1) and H₂ and Pd/C.

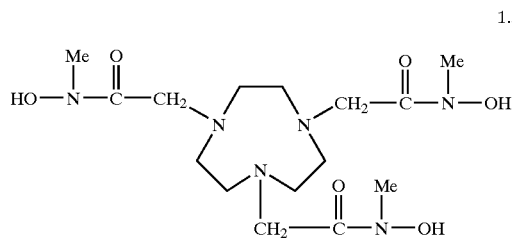

1.3.5.2

1.3.5.3 N,N',N"-Tris[(N-isopropyl-N-benzyloxycarbamoyl)methyl]-1,4,7-triazacyclononane.

From 1,4,7-triazacyclononane trihydrobromide and chloroaceto-N-isopropyl-O-benzyl hydroxamate (1.2.7.2).

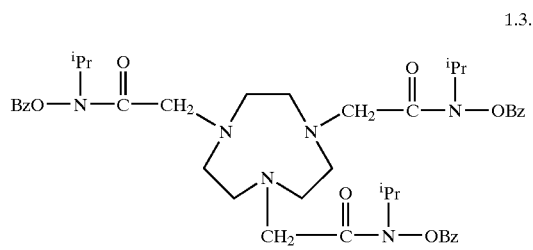

1.3.5.3

1.3.5.4 N,N',N"-Tris[(N-isopropyl-N-hydroxycarbamoyl)methyl]-1,4,7-triazacyclononane.

From 1.3.5.3 and H₂ and Pd/C.

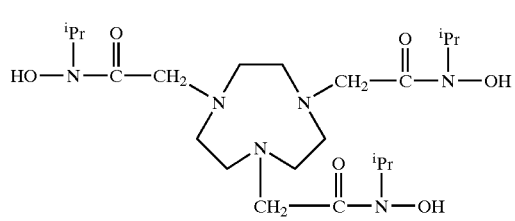

1.3.5.4

1.3.5.5 N,N',N"-Tris[(N-t-butyl-N-benzyloxycarbamoyl)methyl]-1,4,7-triazacyclononane.

From 1,4,7-triazacyclononane trihydrobromide and chloroaceto-N-t-butyl-O-benzyl hydroxamate (1.2.7.3).

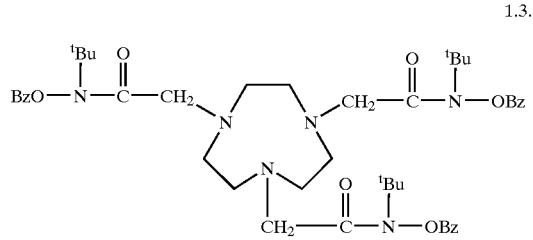

1.3.5.5

1.3.5.6 N,N',N"-Tris[(N-t-butyl-N-hydroxycarbamoyl)methyl]-1,4,7-triazacyclononane.

From 1.3.5.5, H₂ and Pd/C.

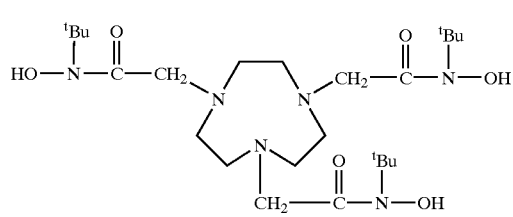

1.3.5.6

1.3.5.7 N,N',N"-Tris[(N-benzyloxycarbamoyl)methyl]-1,4,7-triazacyclononane.

From 1,4,7-triazacyclononane (1.1.3) trihydrobromide and chloroaceto-O-benzyl hydroxamate (1.2.7.4).

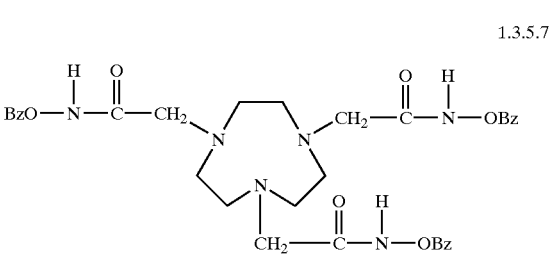

1.3.5.7

1.3.5.8 N,N',N"-Tris[(N-hydroxycarbamoyl)methyl]-1,4,7-triazacyclononane.

From 1.3.5.7 and H₂ and Pd/C.

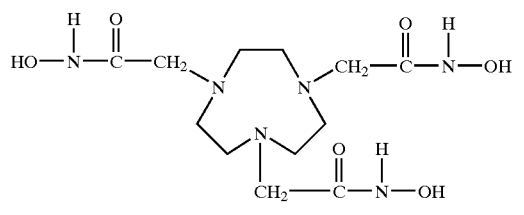

1.3.5.8

1.3.5.9 N,N',N"-Tris[(N-methoxycarbamoyl)methyl]-1,4,7-triazacyclononane.

From 1,4,7-triazacyclononane (1.1.3) trihydrobromide and chloroaceto-O-methyl hydroxamate (1.2.7.5).

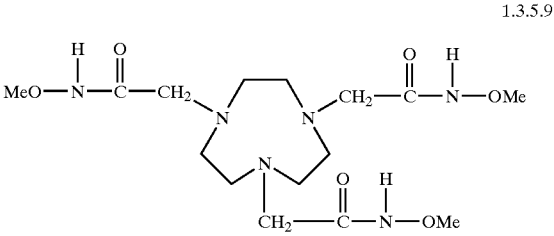

1.3.5.9

1.3.5.10 4,10-Bis[(N-benzyloxycarbamoyl-N-methyl)methyl]-1,4,7,10-tetraazabicyclo[5.5.2]tetradecane.

From 1,4,7,10-tetraazabicyclo[5.5.2]tetradecane (1.1.20) dihydrobromic acid, sodium carbonate and chloroaceto-O-benzyl hydroxamate (1.2.7.4).

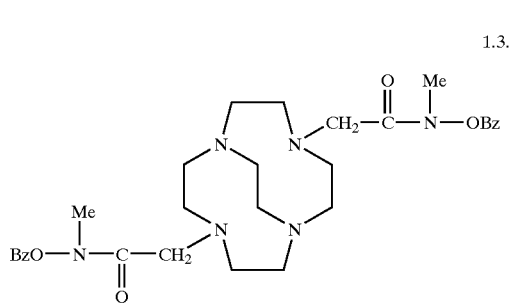

1.3.5.11 4,10-Bis[(N-hydroxycarbamoyl-N-methyl) methyl]-1,4,7,10-Tetraazabicyclo [5.5.2] tetradecane.

From 1.3.5.10 and H₂ and Pd/C.

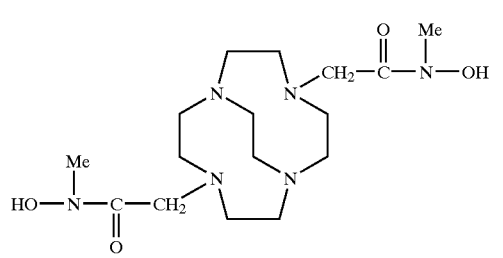

1.3.5.12 N,N',N"-Tris[(1-benzyloxy-2-pyrrolidone-5-yl)methyl]-1,4,7-triazacyclononane.

From 1,4,7-triazacyclononane (1.1.3), 5-(p-toluenesulfonyloxymethyl)-1-benzyloxy-2-pyrrolidone (1.2.6.3) and base.

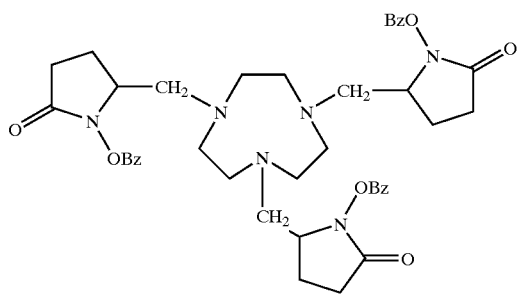

1.3.5.13 N,N',N"-Tris[(1-oxy-2-pyrrolidone-5-yl)methyl]-1,4,7-triazacyclononane.

From 1.3.5.12 and Pd/C (5%) and H₂.

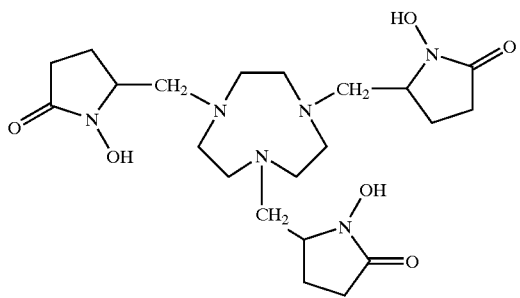

1.3.5.14 N,N',N"-Tris(1-benzyloxy-2-pyrrolidone-5-yl)-1,4,7-triazacyclononane.

From 1,4,7-triazacyclononane (1.1.3), 5-bromo-1-benzyloxy-2-pyrrolidone (1.2.6.11) and base.

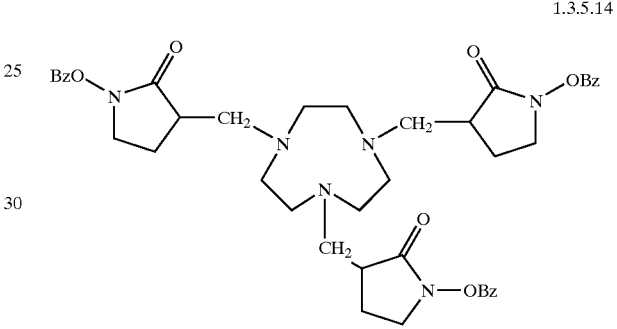

1.3.5.15 N,N',N"-Tris(1-oxy-2-pyrrolidone-5-yl)-1,4,7-triazacyclononane.

From 1.3.5.14 and Pd/C (5%) and H₂

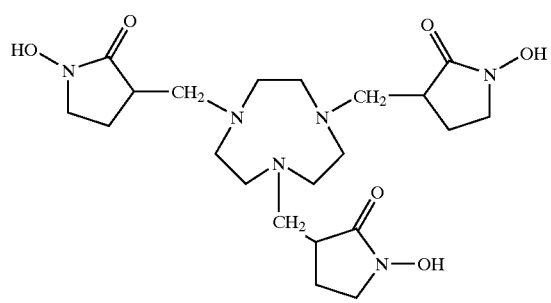

1.3.6 Synthesis of Polyaza Ligands with Pendant Arms Containing Carboxyl Groups And The Corresponding Esters.

Compounds were prepared by reacting polyaza bases with either halo carboxylic acids or by reductive alkylation with aldo or keto acids. The esters were prepared either by reacting directly with halo carboxylic acid esters or by reaction of the free acid with SOCl₂/alcohol.

1.3.6.1 N,N',N"-Tris(carboxymethyl)-1,4,7-triazacyclononane.

From 1,4,7-triazacyclononane (1.1.3), glyoxylic acid and H₂/Pt.

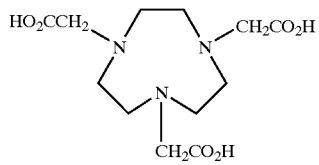

1.3.6.1

1.3.6.2 N,N',N"-Tris(methoxycarbonylmethyl-1,4,7-triazacyclononane.

From N,N',N"-tris(carboxymethyl)-1,4,7-triazacyclononane in methanol and $SOCl_2$.

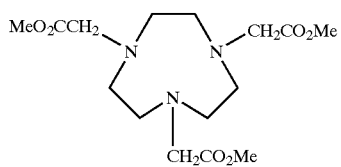

1.3.6.2

1.3.6.3 N,N',N"-Tris(α-methylcarboxymethyl)-1,4,7-Triazacyclononane.

From 1,4,7-triazacyclononane (1.1.3), pyruvic acid and $H_2/Pt$.

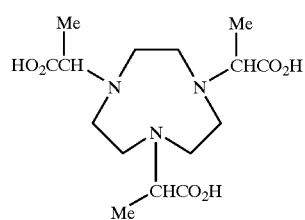

1.3.6.3

1.3.6.4 N,N',N"-Tris(methoxycarbonylmethyl-1,4,7-triazabicyclo-[7.4.0]tridecane.

From 1,4,7-Triazabicyclo[7.4.0]tridecane hydrobromide (1.1.14), glyoxylic acid and $H_2/PtO_2$ in methanol.

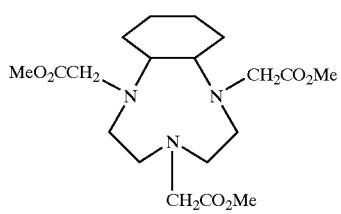

1.3.6.4

1.3.6.5 N-(α-methylcarboxymethyl)-1,4,7-triazabicyclo[7.4.0]tridecane.

From 1,4,7-triazabicyclo[7.4.0]tridecane (1.1.14), pyruvic acid and $H_2/PtO_2$.

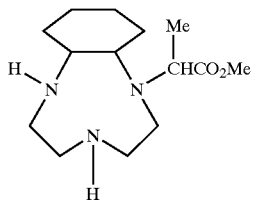

1.3.6.5

1.3.6.6 N,N',N"-Tris(ethoxycarbonylmethyl)-1,4,7-triazacyclo[7.4.0]tridecane.

From 1,4,7-triazabicyclo[7.4.0]tridecane (1.1.14), sodium methoxide and ethyl bromoacetate.

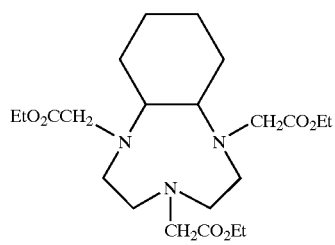

1.3.6.6

1.3.6.7 1,2-Bis-(4,7-carboxymethyl-1,4,7-triazacyclononan-1-yl)ethane.

From 1,2-Bis(1,4,7-triazacyclononan-1-yl)ethane (1.1.28), chloroacetic acid and NaOH.

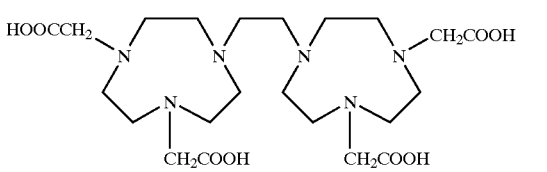

1.3.6.7

1.3.6.8 4,7-Bis(carboxymethyl)-1,4,7,10-tetraazabicyclo[5.5.2]tetradecane.

From 1,4,7,10-tetraazabicyclo[5.5.2]tetradecane (1.1.22), chloroacetic acid and NaOH.

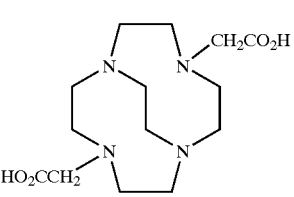

1.3.6.8

1.3.6.9 4,7-Bis(methoxycarboxymethyl)-1,4,7,10-tetraazabicyclo[5.5.2] tetradecane.

From 4,7-bis(carboxymethyl)-1,4,7,10-tetraazabicyclo[5.5.2] tetradecane (1.1.20) in $MeOH/H_2SO_4$.

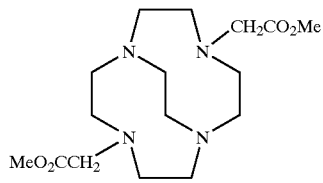
1.3.6.9

1.3.6.10 N,N',N''-Tris(carboxyethyl)-1,4,7-triazacyclononane.

From 1,4,7-triazacyclononane (1.1.3), 3-chloropropionic acid and base.

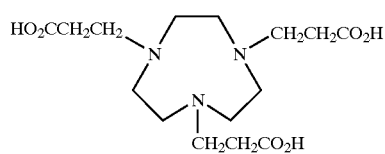
1.3.6.10

1.3.6.11 4,10-Bis(ethoxycarboxymethyl)-1,4,7,10-tetraazabicyclo[5.5.2] tetradecane.

From 1,4,7,10-tetraazabicyclo[5.5.2]tetradecane (1.1.20) and ethyl acrylate.

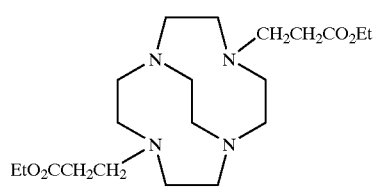
1.3.6.11

1.3.6.12 4,10-Bis(carboxymethyl)-1,4,7,10-tetraazabicyclo[5.5.2]tetradecane.

From 1.3.6.11 by acid hydrolysis.

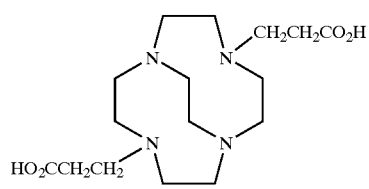
1.3.6.12

1.3.6.13 N,N',N''-Tris(ethoxycarbonylmethyl)-1,4,7-triazacyclononane.

From 1,4,7-triazacyclononane (1.1.3), ethyl bromoacetate and base.

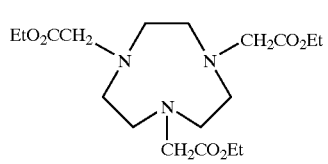
1.3.6.13

1.3.6.14 1,2-Bis-(4,7-methoxycarbonylmethyl-1,4,7-triazacyclononan-1-yl)-ethane.

From 1,2-bis-(4,7-carboxymethyl-1,4,7-Triazacyclononan-1-yl)ethane (1.3.6.7), MeOH/SOCl$_2$.

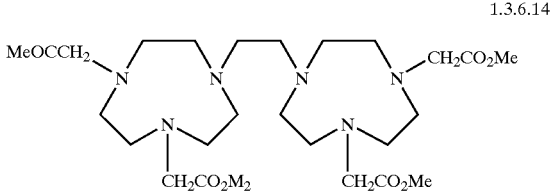
1.3.6.14

1.3.7 Synthesis of Polyaza Ligands with Pendant Arms Containing Aldehyde or Ketone Groups.

1.3.7.1 N,N',N''-Tris(2,2-dimethoxyethyl)-1,4,7-triazacyclononane.

From 1,4,7-triazacyclononane (1.1.3), 1-chloro-2,2-dimethoxyethane (commercially available) and sodium carbonate.

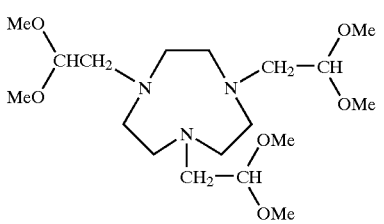
1.3.7.1

1.3.7.2 N,N',N''-Tris-(3,3-dimethyl-2-oxo-butyl)-1,4,7-triazacyclononane.

From 1,4,7-triazacyclononane (1.1.3), bromomethyl t-butyl ketone (commercially available) and sodium carbonate.

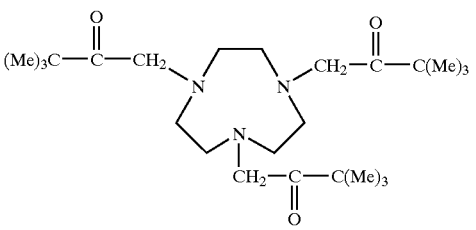
1.3.7.2

1.3.8 Synthesis of Polyaza Ligands with Pendant Arms Containing Pyrrole Groups.

1.3.8.1 N,N',N''-Tris(-pyrrol-2-yl-methyl)-1,4,7-triazacyclononane.

From 1,4,7-triazacyclononane (1.1.3), pyrrole-2-carboxaldehyde (commercially available) and H$_2$/PtO$_2$.

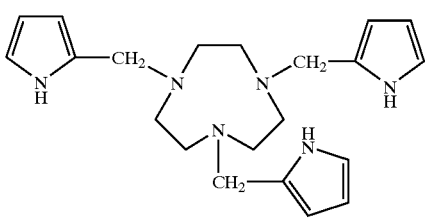
1.3.8.1

1.3.9 Synthesis of Polyaza Ligands with Pendant Arms Containing Amine Groups.

1.3.9.1 N,N',N''-Tris(2-p-toluenesulfonyloxyethyl)-1,4,7-triazacyclononane.

From 1,4,7-triazacyclononane (1.1.3), 2-(p-toluenesulfonylamino)-1-(p-toluenesulfonyloxy)ethane (1.1.16) and base.

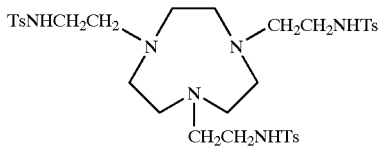

1.3.9.1

1.3.9.2 N,N',N"-Tris(2-aminoethyl)-1,4,7-triazacyclononane.

From 1.3.9.1 and HBr/acetic acid.

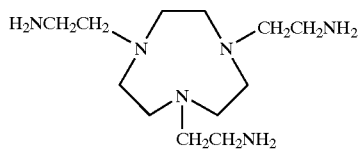

1.3.9.2

1.3.10 Synthesis of Polyaza Ligands with Pendant Arms Containing Amide Groups. 1.3.10.1 N,N',N"-Tris(methylcarboxamide)-1,4,7-triazacyclononane.

From N,N',N"-Tris-(methoxycarboxymethyl)-1,4,7-triazacyclononane (1.3.6.2) and ammonia.

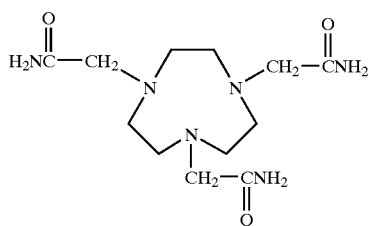

1.3.10.1

1.3.10.2 N,N',N"-Tris[-N-n-butyl(methylcarboxamide)]-1,4,7-triazacyclononane.

From N,N',N"-Tris-(methoxycarboxymethyl)-1,4,7-triazacyclononane (1.3.6.2) and butylamine.

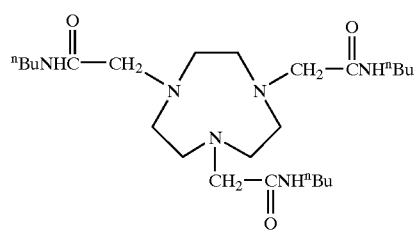

1.3.10.2

1.3.10.3 N,N',N"-Tris[-N-n-phenyl(methylcarboxamide)]-1,4,7-triazacyclononane.

From 1,4,7-triazacyclononane (1.1.3), N-phenylchloroacetamide (prepared from aniline and chloroacetyl chloride) and excess sodium carbonate.

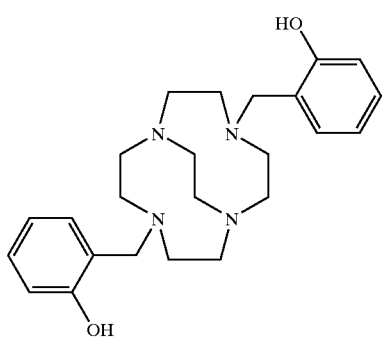

1.3.10.3

1.3.11 Synthesis of Polyaza Ligands with Pendant Arms Containing Phenolic Groups.
1.3.11.1 4,7-Di-(2-hydroxy-benzyl)-1,4,7,10-tetraazabicyclo[5.5.2]tetradecane.

From 1,4,7,10-tetraazabicyclo[5.5.2]tetradecane (1.1.20), salicylaldehyde (excess) and $H_2$/PtO$_2$.

1.3.11.1

1.3.11.2 4-(2-hydroxy-benzyl)-1,4,7,10-tetraazabicyclo[5.5.2]tetradecane.
From 1,4,7,10-tetrazabicyclo[5.5.2]tetradecane (1.1.20), salicylaldehyde (1.5 equivalents) and $H_2$/PtO$_2$.

1.3.11.2

1.3.11.3 Bis-(2,2'-dihydroxybiphenylmethylene) ethylene diamine.
From ethylenediamine (1.1.0) and 2,2'-dihydroxy benzophenone (commercially available) with removal of $H_2O$.

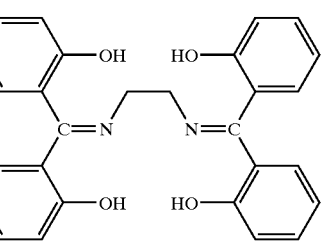

1.3.11.3

1.3.11.4 N,N'-Bis-(2,2'-dihydroxybiphenylmethyl) ethylene diamine.

From 1.3.11.3 and sodium borohydride.

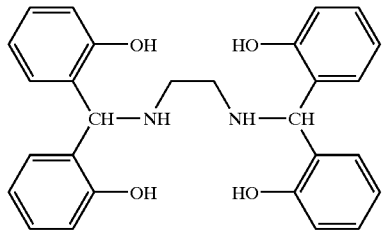
1.3.11.4

1.3.11.5 Bis-(2,4-dihydroxybiphenylmethylene) ethylenediamine.

From ethylenediamine (1.1.0) and 2,4-dihydroxy benzophenone (commercially available) with removal of $H_2O$.

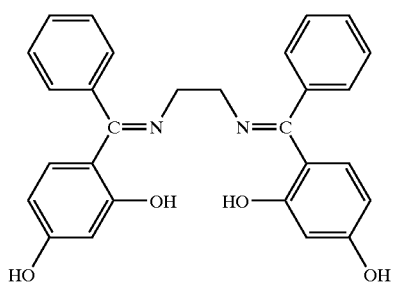
1.3.11.5

1.3.11.6 N,N'-Bis-(2,4-dihydroxybiphenylmethyl) ethylenediamine.

From 1.3.11.5 and sodium borohydride.

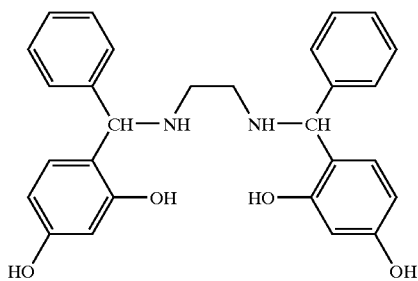
1.3.11.6

1.3.11.7 N,N"-Bis-(2,2'-dihydroxybiphenylmethylene) diethylene triamine.

From diethylene triamine (1.1.1) and 2,2'-dihydroxy benzophenone with removal of $H_2O$.

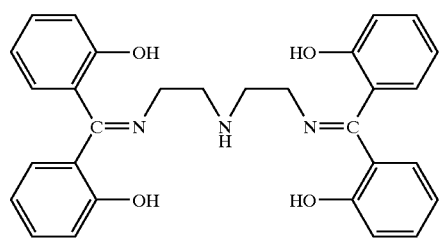
1.3.11.7

1.3.11.8 N,N"-Bis-(2,2'-dihydroxybiphenylmethyl) diethylene triamine.

From 1.3.11.7 and sodium borohydride.

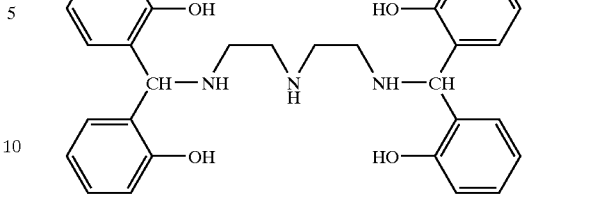
1.3.11.8

1.3.11.9 Bis-(2,2'-dihydroxybiphenylmethylene)-1,3-diaminopropane.

From diaminopropane and 2,2'-dihydroxy benzophenone with removal of $H_2O$.

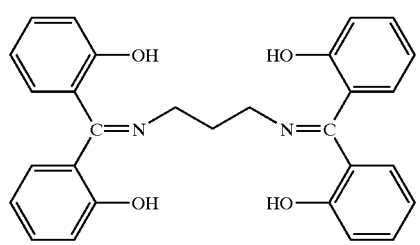
1.3.11.9

11.3.11.10 N,N'-Bis-(2,2'-dihydroxybiphenylmethyl)-1,3-diaminopropane.

From and 1.3.11.9 and sodium borohydride.

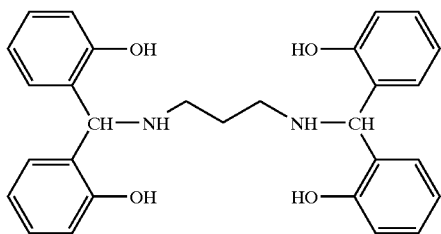
1.3.11.10

1.3.11.11 N,N',N"-Tris(2-hydroxybenzyl)-1,4,7-triazacyclononane.

From 1,4,7-triazacyclononane, salicylaldehyde and $H_2/PtO_2$.

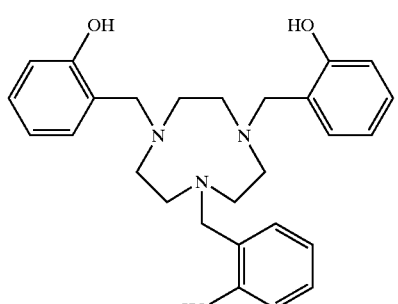
1.3.11.11

1.3.12 Synthesis of Polyaza Ligands with More Than One Species of Pendant Arm.

1.3.12.1 N-(p-Toluenesulfonyl)-N', N"-bis(diethylphosphorylmethyl)-1,4,7-triazacyclononane.

From N-(p-toluenesulfonyl)-1,4,7-triazacyclononane dihydrobromide (1.3.13.31), formaldehyde and diethyl phosphite.

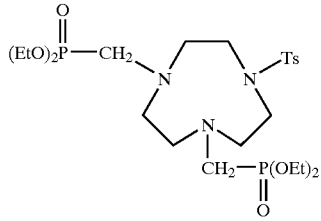

1.3.12.2 N,N'-Bis(diethylphosphorylmethyl)-1,4,7-triazacyclononane.

From 1,4,7-triazacyclononane (1.1.3) trihydrobromide, one equivalent formaldehyde and one equivalent of diethyl phosphite. Purification of product by chromatography.

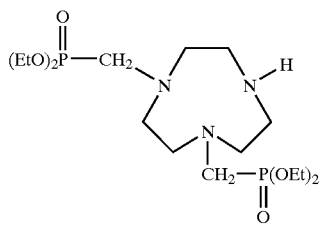

1.3.12.3 N,N'-Bis(dihydroxyphosphorylmethyl)-1,4,7-triazacyclononane.
From 1.3.12.2 and HCl.

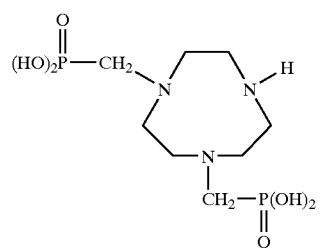

1.3.12.4 N-(Carboxymethyl)-N,N'-bis(dihydroxyphosphorylmethyl)-1,4,7-triazacyclononane.
From 1.3.12.3, chloroacetic and NaOH,

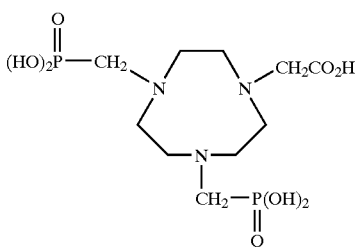

1.3.12.5 4-(2-Hydroxy-benzyl)-7-diethylphosphorylethyl-1,4,7,10-tetraazabicyclo[5.5.2]tetradecane.

From 4-(2-hydroxybenzyl)-1,4,7,10-tetraazabicyclo[5.5.2]tetradecane (1.3.11.2), diethyl phosphite and formaldehyde solution.

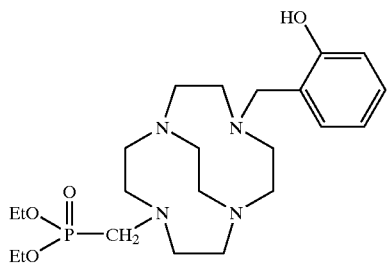

1.3.12.6 4-(2-hydroxy-benzyl)-7-phosphorylethyl-1,4,7,10-tetraazabicyclo[5.5.2]tetradecane.
From 1.3.12.5 and HCl.

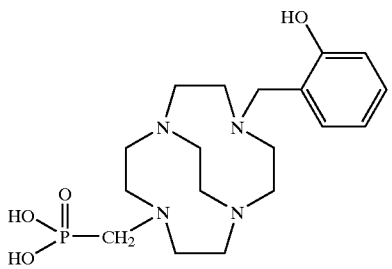

1.3.13 Miscellaneous Substituted Polyaza Compounds.

1.3.13.1 1,2-Bis-(4,7-benzyloxycarbonyl-1,4,7-triazacyclononan-1-yl)ethane.

From 1,2-bis-(1,4,7-triazacyclononan-1-yl)ethane(1.1.28) polyhydrobromide, potassium carbonate and benzyl chloroformate.

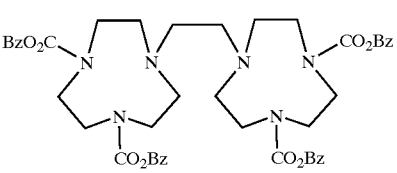

1.3.13.2 N-(p-Toluenesulfonyl)-N',N''-Bis-(benzyloxycarbonyl)-1,4,7-triazacyclononane.

From N-(p-toluenesulfonyl)-1,4,7-triazacyclononane dihydrobromide (1.3.13.31), K₂CO₃ and benzyl chloroformate.

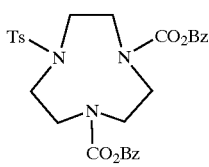

1.3.13.3 N-(p-Toluenesulfonyl)-N''-benzyloxycarbonyl-1,4,7-triazacyclononane.

From N-(p-toluenesulfonyl)-N',N''-bis(benzyloxycarbonyl)-1,4,7-triazacyclononane (1.3.13.2) and trimethylsilyl iodide.

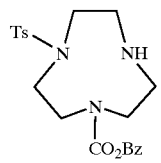

1.3.13.3

1.3.13.4 1,2-Bis[(1-p-toluenesulfonyl)-4-benzyloxycarbonyl-1,4,7-triazacyclononan-7-yl]ethane.

From 1-(p-toluenesulfonyl)-4-benzyloxycarbonyl-1,4,7-triazacyclononane (1.3.13.3), potassium carbonate and dibromoethane.

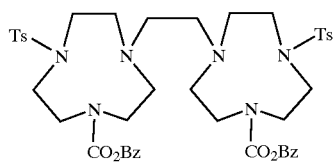

1.3.13.4

1.3.13.5 N,N',N''-Tris(phenylacetyl)-1,4,7-triazacyclononane.

From 1,4,7-triazacyclononane (1.1.3), diethyl phenylacetylphosphonate

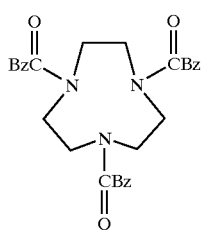

1.3.13.5

1.3.13.6 N,N',N''-Tris(2,3-Epoxypropyl-1,4,7-Triazacyclononane.

From 1,4,7-triazacyclononane (1.1.3) and epibromohydrin.

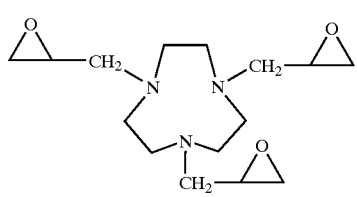

1.3.13.6

1.3.13.7 N,N',N''-Tri-allyl-1,4,7-triazacyclononane.

From 1,4,7-triazacyclononane (1.1.3), sodium hydride and allyl bromide.

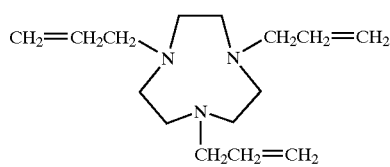

1.3.13.7

1.3.13.8 N,N',N''-Tris(benzyloxycarbonyl)-1,4,7-triazacyclononane.

From 1,4,7-triazacyclononane (1.1.3), benzyl chloroformate and sodium carbonate.

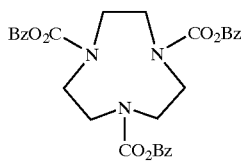

1.3.13.8

1.3.13.9 N,N'-Bis(benzyloxycarbonyl)-1,4,7-triazacyclononane.

From N,N',N''-tris(benzyloxycarbonyl)-1,4,7-triazacyclononane (1.3.13.8) and iodotrimethylsilane.

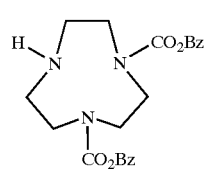

1.3.13.9

1.3.13.10 N,N'-Bis(benzyloxycarbonyl)-N''-(2-bromoethyl)-1,4,7-triazacyclononane.

From N,N'-bis(benzyloxycarbonyl)-1,4,7-triazacyclononane (1.3.13.9), dibromoethane and potassium carbonate.

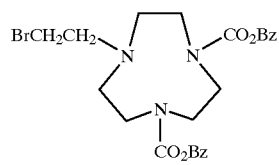

1.3.13.10

1.3.13.11 N-p-Toluenesulfonyl-N',N''-ditrifluoroacetyl-1,4,7-triazacyclononane.

From N-p-toluenesulfonyl-1,4,7-triazacyclononane (1.3.13.31), potassium carbonate and trifluoroacetic anhydride.

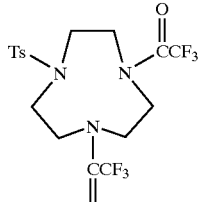

1.3.13.11

1.3.13.12 N-p-Toluenesulfonyl-N'-benzyl-1,4,7-triazacyclononane.

From N-(p-toluenesulfonyl-1,4,7-triazacyclononane (1.3.13.31), sodium hydride and benzyl bromide.

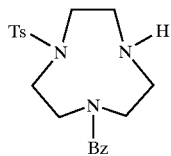
1.3.13.12

1.3.13.13 N-p-Toluenesulfonyl-N',N''-dibenzyl-1,4,7-triazacyclononane.

From N-(p-toluenesulfonyl-1,4,7-triazacyclononane (1.3.13.31), sodium hydride and benzyl bromide.

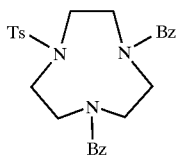
1.3.13.13

1.3.13.14 1,2-Bis(N-p-toluenesulfonyl-N'-benzyl)-1,4,7-triazacyclononan-1-yl) ethane.

From N-p-toluenesulfonyl-N'-benzyl-1,4,7-triazacyclononane (1.3.13.12), dibromoethane and potassium carbonate.

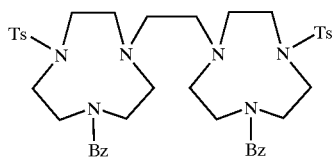
1.3.13.14

1.3.13.15 1,2-Bis(N,N'-ditrityl-1,4,7-triazacyclononan-1-yl) ethane.

From 1,2-Bis(1,4,7-triazacyclononane)ethane (1.1.28), potassium carbonate and trityl chloride.

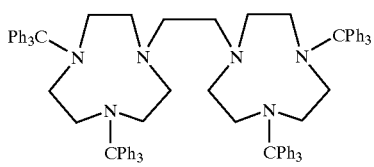
1.3.13.15

1.3.13.16 Spiro [4,8]-4,7-di-p-toluenesulfonyl-4,7-diaza-1-azotridecane halide.

From 1,4,7-triazacyclononane-N,N'-di-p-toluenesulfonyl hydrobromide (1.3.13.32), diiodobutane and potassium carbonate.

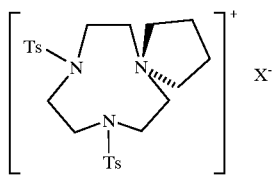
1.3.13.16

1.3.13.17 Tetrakis(p-toluenesulfonyl)-1,4,7,10-tetraazacyclotetradecane.

From N,N',N''-tris(p-toluenesulfonyl)diethylenetriamine (1.3.13.18), potassium carbonate and bis(2-p-toluenesulfonyloxyethyl)-N-(p-toluenesulfonyl) amine (1.3.13.19).

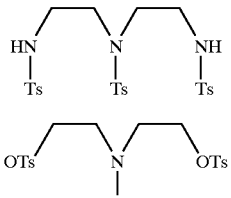
1.3.13.18

1.3.13.19

1.3.13.17

11.3.13.20 1,7-Bis(p-toluenesulfonyl)-4-benzyl-1,4,7-triazaheptane.

From benzylamine, (2-p-toluenesulfonyoxyl)-N-(p-toluenesulfonyl)-ethylamine (1.3.13.21) and potassium carbonate.

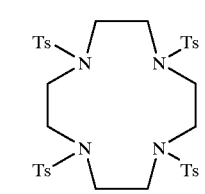
1.3.13.21

1.3.13.20

1.3.13.22 N-Trityldiethanolamine.

From diethanolamine and trityl chloride.

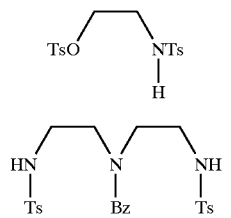
1.3.13.22

1.3.13.23 N-Trityl-bis(2-p-toluenesulfonyloxyethyl)amine.

From N-trityldiethanolamine and p-toluenesulfonyl chloride.

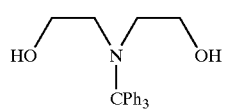
1.3.13.23

1.3.13.24 1,7-di-(p-toluenesulfonyl)-4-benzyl-10-trityl-1,4,7,10-tetraazacyclotetradecane.

From 1,7-di-p-toluenesulfonyl-4-benzyl-1,4,7-triazaheptane (1.3.13.20), sodium hydride and N-trityl-di-p-toluenesulfonyldiethanolamine (1.3.13.23).

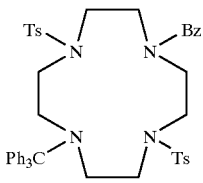

1.3.13.24

1.3.13.25 1,7-Di-(p-toluenesulfonyl)-1,4,7,10-tetraazacyclotetradecane.

From 1,7-di-(p-toluenesulfonyl)-4-benzyl-10-trityl-1,4,7,10-tetraazacyclotetradecane (1.3.13.24) reduced by $H_2$ and Pd/C.

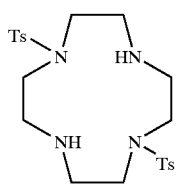

1.3.13.25

1.3.13.26 1,7-Di-(p-toluenesulfonyl)-4-benzyl-1,4,7,10-tetraazacyclotetradecane.
From reduction of 1.3.13.24.

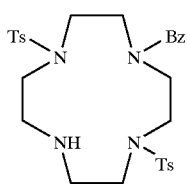

1.3.13.26

1.3.13.27 1,2-Bis-(4,10-di-p-toluenesulfonyl-7-benzyl-1,4,7,10-tetraazacyclotetradecane-1-yl)ethane.
From 1.3.13.26 and dibromoethane.

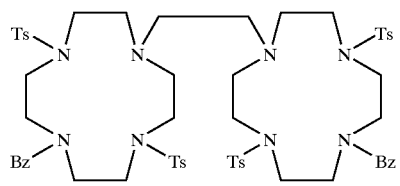

1.3.13.27

1.3.13.28 1,5,9,13-Tetraazatetracyclo[6,6,2,0$^{1,15}$, 0$^{8,16}$]hexadecane
From 1.1.6 and glyoxaldehyde.

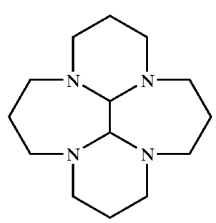

1.1.6

1.3.13.29 4,7-Diallyl-1,4,7-triazabicyclo[7,4,0]tridecane.
From 1,4,7-triazabicyclo[7,4,0]tridecane trihydrobromide (1.1.14), sodium hydride and allyl bromide.

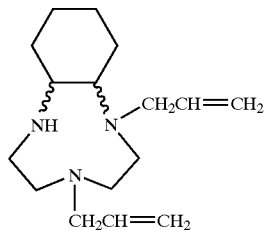

1.3.13.29

1.3.13.30 N-p-Toluenesulfonyl-1,4,7-triazacyclononane dihydrobromide.

From N,N',N"-Tris(p-toluenesulfonyl)-1,4,7-triazacyclononane (1.3.13.31) prepared from 1.3.13.18, dibromoethane and base) and HBr/acetic acid.

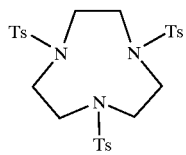

1.3.13.31

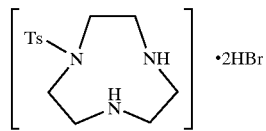

1.3.13.30

1.3.13.32 N,N'-Di-p-Toluenesulfonyl-1,4,7-triazacyclononane hydrobromide.

a) From N,N',N"-tris(p-toluenesulfonyl)-1,4,7-triazacyclononane (1.3.13.31 and HBr/acetic acid as the hydrobromide salt.

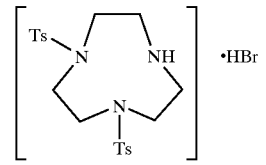

1.3.13.32

1.3.13.33 N,N,N',N'-Tetraallylethylenediamine.

From ethylenediamine, sodium carbonate and allyl bromide.

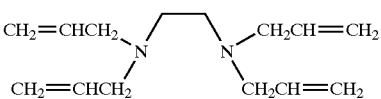

1.3.13.33

1.3.13.34 4,7,13-Tris(p-toluenesulfonyl)-1,4,7,10-13-pentaazabicyclo[8.5.2]heptadecane.

From 1,4,7,10,13-pentaazabicyclo[8.5.2]heptadecane (1.1.26), potassium carbonate and p-toluenesulfonyl chloride.

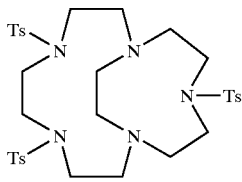

1.3.13.35 1,2-Bis(4-p-toluenesulfonyl-1,4,7-triazacyclononan-1-yl)ethane.

From 1,2-bis(4,7-di-p-toluenesulfonyl-1,4,7-triazacyclononane-1-yl)ethane (1.1.30) and sulphuric acid.

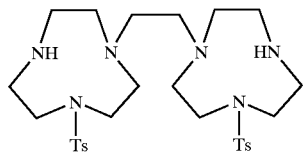

1.3.13.36 N,N'-(Di-p-toluenesulfonyl)-N''-benzyl-1,4,7-Triazacyclononane.
a) From N,N''-(p-toluenesulfonyl)-4-benzyl diethylenetriamine (1.3.13.20), sodium hydride and ethylene glycol di-p-toluenesulfonate (1.1.12).
b) From N,N'-bis(p-toluenesulfonyl)-1,4,7-triazacyclononane (1.3.13.32), sodium hydride and benzyl bromide.

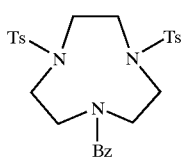

1.3.13.37 N-(p-Toluenesulfonyl)-N'-trityl-1,4,7-triazacyclononane.

From N-(p-toluenesulfonyl-1,4,7-triazacyclononane dihydrobromide (1.3.13.30), sodium hydride and trityl chloride.

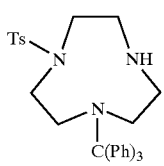

1.3.13.38 Hexakis(allyl) triethylenetetramine.

From triethylenetetramine (1.1.2), sodium carbonate and allyl bromide.

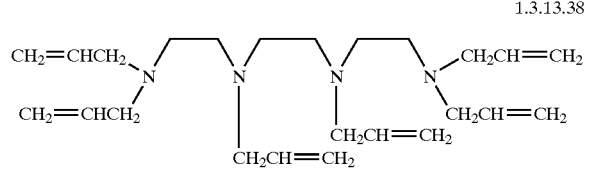

1.3.13.39 4,7-diallyl-1,4,7,10-tetraazabicyclo[5.5.2]tetradecane.

From 1,4,7,10-tetraazabicyclo[5.5.2]tetradecane (1.1.4), allyl bromide and base.

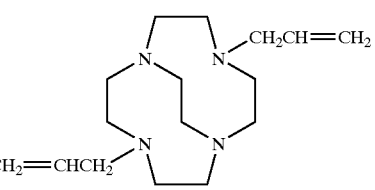

EXAMPLE 2

This example illustrates the relatively low toxicity of a representative example of the chelators of this invention toward nonproliferating mammalian cells in vitro.

N,N',N''-tris(dihydroxyphosphorylmethyl)-1,4,7-triazacyclononane was prepared as described in Example 1C of U.S. Pat. No. 5,236,695.

A concentration of 0.3 mM of this agent was added to mature, nonreplicating cultures of HFF (human foreskin fibroblasts) kept in maintenance media, and no effect on the resting cells was observed over a five-day period of observation.

EXAMPLE 3

This example illustrates the low in vivo toxicity of a representative example of the chelators of this invention upon administration to mice.

Over 50% of the mice receiving 3.0 mM/kg intravenously of the sodium salt of N,N',N''-tris (dihydroxyphosphorylmethyl)-1,4,7-triazacyclononane (Example-1 C of U.S. Pat. No. 5,236,695) as a single intravenous dose survived for over 14 days following such administration, thus demonstrating that the acute $LD_{50}$ of this agent is in excess of 3.0 mM/kg. This in vivo $LD_{50}$ toxicity dose results in an instantaneous in vivo concentration which is orders of magnitude greater than the dose of this agent which inhibits mammalian cell replication in vitro (0.009 mM/L).

EXAMPLE 4

This example demonstrates the relatively subacute toxicity of a representative example of the chelators of this invention upon administration intravenously in repeated doses to rats.

Ten male Sprague Dawley rats 29 days old and weighing between 73.4 and 87.8 grams at the beginning of the experiment were randomized, employing the block stratificaton method, into two groups consisting of five rats each. On each of days 1, 2, 3, 6, 7, 8, 9, 10, 13 and 14 of the experiment one set of rats received an intravenous dose of N,N',N''-tri(dihydroxyphosphoryl methyl)-1,4,7-triazacyclononane (Example 1C in U.S. Pat. No. 5,236,695) equal to 0.05 millimoles per kg of initial body weight (experimental group) while the other group received an equivalent volume of normal saline solution. The weights of the animals were recorded three times per week and the animals were sacrificed on the 28th day, major organs removed and weighed and tissues removed for microscopic examination. There was no statistically significant difference in weight or rate of weight gain between the experimental and control group of rats, either during the period of injections or in the two-week post-injection period. There were no differences observed between the weights of major organs of the experimental vs. the control group. There were no differences between the tissues of the experimental vs. the control group upon microscopic examination of the tissues obtained at the time of necropsy.

EXAMPLE 5

This example demonstrates the inhibition of iron-catalyzed free radical generation through Fenton Reactions (iron catalyzed Haber-Weiss pathways).

Employing published methods, as described in "Quantitative Effects of Iron Chelators on Hydroxyl Radical Production by the Superoxide-Driven Fenton Reaction," J. B. Smith, J. C. Cusumano, C. F. Babbs, *Free Rad. Res. Comms.* 1990, Vol. 8, No. 2, 101–106, the ability of Fe(III) complexed to N,N',N"-tri(dihydroxy-phosphoryl methyl)-1,4,7-triazacyclononane to support Fenton reactions was evaluated. Fe(III) complexed by EDTA was used as a positive control and supported the Fenton reaction yielding hydroxyl radicals while Fe(III) complexed to 3 MP failed to show evidence of hydroxyl ion formation above background.

EXAMPLE 6

This example demonstrates the cardioprotection afforded by physiological salts of N,N',N"-tris(dihydroxyphosphorylmethyl)-1,4,7-triazacyclononane (referred to below as "the test compound") following ischemia in ex-vivo working rat hearts and in unanesthetized and anesthetized rabbits.

Description of the Studies

Cardiac functional parameters were evaluated prior to, and following, global ischemia in the ex vivo working rat heart model and prior to, and following, rapid ventricular overdrive pacing [VOP] induced ischemia in vivo in the unanesthetized rabbit model. Measured cardiac performance parameters included heart rate, coronary flow, aortic flow, cardiac output, left ventricular developed pressure, maximum and minimum of first derivative of left ventricular pressure, left ventricular end-diastolic pressure, and incidence of ventricular fibrillation. In the VOP induced ischemia unanesthetized rabbit model, intracavitary EKG patterns were also monitored. Use of the ex vivo working rat heart model allowed for evaluation of the effects of the test compound at various fixed concentrations in the perfusing medium on cardiac functional parameters prior to, and following ischemic stress. This model also allowed for a comparison of such effects when deferoxamine vs. the test compound was present at various concentrations in the perfusing medium. Use of the VOP-induced ischemia unanesthetized rabbit model allowed for monitoring in vivo effects of the test compound in the absence of anesthesia prior to, and following, reversible ischemia. The ability of the test compound to decrease the volume of infarcted myocardium was evaluated in the anesthetized rabbit model. In these later studies the potent potassium channel opening, nitric oxide releasing, agent, nicorandil, was used as a positive control.

Summary of Study Findings

In the ex vivo working rat heart model, addition of the test compound to the perfusing medium was shown to be significantly cardioprotective with regard to cardiac performance parameters following global ischemia. Cardioprotection following ischemia was observed over a broad concentration range of the compound. Peak efficacy was observed at 0.01 mM concentration. Concentrations as high as 2.7 mM had no effects on cardiac performance parameters prior to ischemia and had no adverse effects following ischemia. In similar studies employing deferoxamine, some modest cardioprotective effects following ischemic stress were observed at 0.9 mM but no cardioprotective effects were observed at concentrations of <0.9 mM deferoxamine. Concentrations of 2.7 mM deferoxamine had adverse effects on cardiac functional parameters both prior to, and following, ischemia. These data demonstrate cardioprotective properties and cardiac tolerance of the test compound in the working ex vivo rat heart model of reversible global ischemia and a high absolute cardiac tolerance to the test compound. The cardioprotective properties of the test compound could not be attributed to alterations in cardiac work load or myocardial perfusion prior to ischemia since the test compound had no affect on cardiac performance parameters prior to ischemia.

In the in vivo unanesthetized rabbit VOP-induced myocardial ischemia model, intravenous doses of 0.032 mmole/kg and 0.096 mmole/kg of the test compound were cardioprotective with regard to cardiac performance parameters when administered 10 min prior to VOP. A single IV dose of 0.032 mmole/kg of the test compound demonstrated significant cardioprotection when administered up to 60–120 min prior to VOP-induced ischemia. The test compound had no affect on any cardiac performance parameters in these experiments prior to VOP-induced ischemia. These data demonstrate a high cardiac tolerance for the test compound and a prolonged cardioprotective effect of the test compound following its administration in the unanesthetized rabbit VOP model of reversible ischemia that is not mediated by pre-ischemia alterations in myocardial workload or myocardial perfusion.

Cardioprotection by the test compound in ischemia-reperfusion injury was evaluated in a rabbit myocardial infarction model employing 30 minutes of reversible ligature occlusion of the left anterior descending coronary artery (LCAO) followed by reperfusion for ~24 hours prior to sacrifice. Administration of the test compound beginning after 15 minutes of LCAO resulted in a significant reduction in the volume of infarcted myocardium vs. controls (volume of infarcted myocardium expressed as % of myocardial volume at risk in rabbits teated with the test compound was 30.6%, (SEM=2.7%) vs. saline treated controls of 43.7%, (SEM=3.7%)). Similar cardioprotection was observed when administration of the test compound was initiated 10 minutes prior to the onset of ischemia (infarcted myocardium as a % of volume at risk in Ferofix treated rats=28.1%, (SEM=3.2%), vs. saline control values of 41.7%, (SEM=3.5%)). Cardioprotection by the test compound was achieved without affecting pre-ischemia cardiac performance parameters. In positive control studies administration of nicorandil failed to provide cardioprotection when administered beginning after 15 minutes of LCAO. When nicorandil was administered 10 minutes prior to onset of LCAO, cardioprotection was similar to that observed with the test compound.

These data demonstrate a high cardiac tolerance of the test compound and the cardioprotective effects of the test compound following reversible ischemia in ex vivo and in vivo models as measured by cardiac functional parameters. Administration of the test compound either following onset of ischemia or prior to onset of ischemia was shown to be cardioprotective in vivo following irreversible ischemia as measured by a decrease in the volume of infarcted myocardium. The test compound did not affect cardiac functional parameters prior to onset of ischemia. In contrast, the potent cardioprotective agent, nicorandil, which is not a chelator of first transition series metal cations failed to provide cardioprotection when administered following onset of ischemia. In the ex vivo rat heart model deferoxamine was not well tolerated by the myocardium prior to, and following, ischemia, and showed minimal cardioprotection over a much narrower concentration range than was observed with the test compound.

EXAMPLE 7

This example demonstrates the neuroprotection afforded by physiological salts of N,N',N"-tris (dihydroxyphosphorylmethyl)-1,4,7-triazacyclononane (referred to below as "the test compound") following ischemia in rats.

Materials and Methods

Stroke model: Rats were intubated and anesthetized with Isoflurane 1.5%. The right femoral artery was canulated for invasive monitoring of blood pressure (Biopac MP 100-TSD104A, Biopac Systems, Santa Barbara, Calif., USA). Temperature, heart rate and oxygen saturation were measured throughout the experiment and for 3–4 hours after drug administration using external sensors (Biopac Oxy 100 and SKT 100, Biopac Systems). The right common, external and internal carotid arteries were isolated through a midline neck dissection. The pterygopalatine branch was ligated and a loose suture was placed over the common carotid. The distal external carotid artery was ligated. A 4-0 nylon monofilament suture (Harvard Apparatus) coated with poly-L-Lysine with its tip rounded by heating near a flame was inserted into the external carotid artery through a small arteriotomy and advanced for 19 mm into the internal carotid until occluding the proximal middle cerebral artery. The animals were then allowed to awaken spontaneously and were tested with the motor disability scale detailed below. Only animals showing moderate to severe disability (scores of 5 and above) were included in the study. The animals were re-anesthetized and intubated 120 minutes after filament insertion and the occluding filament was withdrawn at this time. This typically results in transient occlusion of the middle cerebral artery (TMCAO) yielding a large infarct involving cortical and subcortical zones.

Drug administration: In the initial set of experiments (designated below as "Test Compound Set I"), the animals were injected IV with three (3) consecutive doses of the test compound of 0.032 mmoles/kg each, administered at 10 minutes prior to MCA occlusion, 60 minutes after MCA occlusion and at initiation of reperfusion (i.e. after 120 minutes of MCA occlusion). Another group of animals (designated below as "Test Compound Set II") were injected with the test compound or vehicle (designated below as "Vehicle B") at the same dose but at time points of 60 minutes after MCA occlusion, at the time of initiation of reperfusion and 60 minutes after the onset of reperfusion (i.e. 120 min & 180 min after MCA occlusion). Another group of animals were given a single 0.032 mmoles/kg dose of the test compound (designated below as "Test Compound Set III"), or saline vehicle (designated below as "Vehicle A") after 60 minutes of MCA occlusion. A final group of animals were given a single 0.032 mmoles/kg dose of the test compound (designated below as "Test Compound Set IV") after 90 minutes of MCA occlusion. All IV injections were performed while the animals were anesthetized. Groups receiving multiple injections of the test compound (Test Compound Sets I and II and Vehicle B) required repeated administration of anesthetic. Groups receiving one injection (Test Compound Sets III and IV and Vehicle A) did not require administration of additional anesthetic agent other than that required to perform the underlying ischemia-reperfusion study. Motor disability and infarct volume measurements were determined as detailed below.

Motor-disability evaluation: All evaluations were performed employing a standardized motor disability score, as described by Lavie, G., et al., "Long term cerebroprotective effects of dexanabinol in a model of cerebral ischemia," *Brain Res* 901, 195–201 (2001), with slight modifications. The evaluations at 24 hours and 48 hours post ischemia were performed blindly by one of the investigators not aware of the treatment regimen assigned to the animals. Animals were scored 1 point for each of the following parameters: flexion of the forelimb contralateral to the stroke when momentarily hung by the tail, extension of the contralateral hind limb when pulled from table, and rotation to the paretic side against resistance. One (1) point was scored for circling motion to the paretic side when attempting to walk, 1 point for failure to walk out of a circle 50 cm in diameter within 10 seconds, 2 points for failure to leave the circle within 20 seconds and 3 points for inability to exit the circle within 60 seconds. One (1) point each was scored for inability to extend the paretic forepaw when gently pushed against the table from above, laterally and sideways. Thus, an animal with a maximal deficit scored 10 points and an animal with no deficit scored 0 points.

Injury size: Forty-eight hours after the surgery, the animals were re-anesthetized and sacrificed with excess Phenobarbital injected into the heart. The brain was carefully removed and sliced to 2 mm slices using a mold. The slices were stained with 2,3,5-triphenyltetrazolium chloride (TTC, 2% solution in PBS) for 8 hours and preserved in 3.7% formaldehyde. They were photographed on line with an image acquirement system (Lis-700, APPLItec, Rehovot, Israel). Estimation of the lesioned area was performed with an image analysis software (Sigma Scan Pro, SPSS Inc., Richmond, Calif., USA). The volume of injured tissue was divided by that of the contralateral hemisphere in order to control for edema formation. The results were expressed as a percentage of whole hemispheric tissue.

Results:

Physiologic parameters: Animals in all groups treated with the test compound had similar blood pressure, heart rate and temperature values to those of vehicle-treated animals. In all groups cerebral blood flow fell to 16% of pre-ischemic values upon suture insertion and remained so for 2 hours after which it returned towards normal values after suture removal. The weights, motor scores, and infarct volumes for each of the two vehicle groups and four test compound groups are shown in the table below, which lists the mean followed by the standard deviation (following the ± sign) with the SEM in parentheses:

Neuroprotection Study Results

|  | Vehicle A | Vehicle B | Test Compound Set I | Test Compound Set II | Test Compound Set III | Test Compound Set IV |
|---|---|---|---|---|---|---|
| Weight at Baseline | 333 ± 12.0 (4.0) | 364.9 ± 11.8 (3.7) | 333.9 ± 11.9 (4.0) | 311 ± 23.6 (7.5) | 302.3 ± 5.1 (2.1) | 341.43 ± 14.9 (5.6) |
| Motor Score: 1 Hour | 7.7 ± 1.6 (0.5) | 6.3 ± 1.3 (0.4) | 7.3 ± 1.3 (0.4) | 6.9 ± 1.1 (0.4) | 6.8 ± 1.0 (0.4) | 2 hours: 7.43 ± 1.27 (0.48) |
| Motor Score: 24 Hours | 5.6 ± 2.6 (0.9) | 6.8 ± 1.7 (0.5) | 5.9 ± 1.1 (0.4) | 3.6 ± 2.9 (0.9) | 4.3 ± 1.0 (0.4) | 4.9 ± 2.04 (0.77) |
| Motor Score: 48 Hours | 6.3 ± 2.6 (0.9) | 7.3 ± 1.9 (0.6) | 5.4 ± 1.9 (0.7) | 3.0 ± 3.0 (0.9) | 2.8 ± 2.1 (0.9) | 3.7 ± 1.98 (0.75) |
| Infarct Volumes | 19.5 ± 15.7 (5.2) | 19.5 ± 10.5 (3.3) | 3.5 ± 3.7 (1.2) | 6.2 ± 7.5 (2.4) | 2.6 ± 2.1 (0.9) | 4.63 ± 9.08 (3.43) |

Further results are shown in the Figures, which are photographs of typical sections of rat brain in the "Vehicle A" control group (FIG. 1) and in Test Compound Set III (FIG. 2) which involved one dose of 0.03 mmoles/kg administered after sixty minutes of ischemia. White, non-staining areas in these sections indicated infarcted tissue.

The Figures indicate the following:

1. The infarct volumes of the two control groups (Vehicle A and Vehicle B) were similar to published values for control groups employing this model of ischemia-reperfusion.

2. The reduction in infarct volumes in all rats treated with the test compound was robust compared to the corresponding control group and exceeded values reported in the literature employing other neuroprotective agents.

3. The observation that a single 0.032 mmole/kg dose of the test compound provided similar neuroprotection when administered after 60 minutes or 90 minutes of ischemia as that observed when three doses of 0.032 mmoles/kg each were administered at 10 minutes prior to, and 60 minutes post MCA occlusion and at the time of onset of reperfusion, as well as when three doses were administered 60 minutes after MCA occlusion and at the time of onset of reperfusion and 60 minutes after onset of reperfusion, suggests that the principle neuroprotective effect afforded by the test compound in this model in these studies is provided by a single dose of the test compound at 60 minutes or 90 minutes following the onset of MCA occlusion and that little additional neuroprotective effect was afforded by dose administration prior to onset of ischemia, or at the time of onset of reperfusion, or 60 minutes after onset of reperfusion.

The chelator employed in Examples 2, 3, 4, 5, 6, and 7 has thermodynamic equilibrium dissociation constants with $Fe^{+3}$ of $<2.5\times10^{-30}$, with $Cu^{+2}$ of $5.0\times10^{-22}$, with $Zn^{+2}$ of $1.3\times10^{-25}$ and with $Ca^{+2}$ of $4.2\times10^{-7}$.

The foregoing is offered primarily for purposes of illustration. Further variations, modifications, and embodiments that still fall within the spirit and scope of the invention will be readily apparent to those skilled in the art.

What is claimed is:

1. A method for mitigating damage to the central nervous system caused by an ischemic stroke, seizure or trauma in a patient suffering therefrom, said method comprising administering to said patient an effective amount of a chelator that forms a complex with a member selected from the group consisting of cations of iron, copper and zinc, said complex having a thermodynamic equilibrium constant of $10^{-18}$ or less.

2. A method for mitigating damage to the heart caused by a heart attack or arrhythmia in a patient suffering therefrom, said method comprising administering to said patient an effective amount of a chelator that forms a complex with a member selected from the group consisting of cations of iron, copper and zinc, said complex having a thermodynamic equilibrium constant of $10^{-18}$ or less.

3. The method of claims 1 or 2 wherein said chelator has the formula

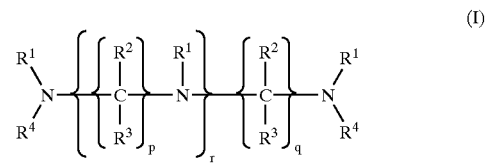

(I)

wherein, p and q are independently integers of from 2 to 3;

r is an integer of from 1 to 4;

$R^2$, $R^3$, and $R^4$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^1$ is a member selected from the group consisting of $R^2$, $R^3$, $R^4$, and radicals of the formula:

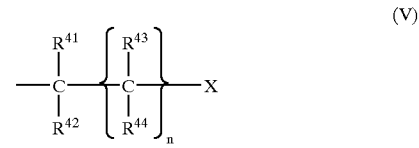

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

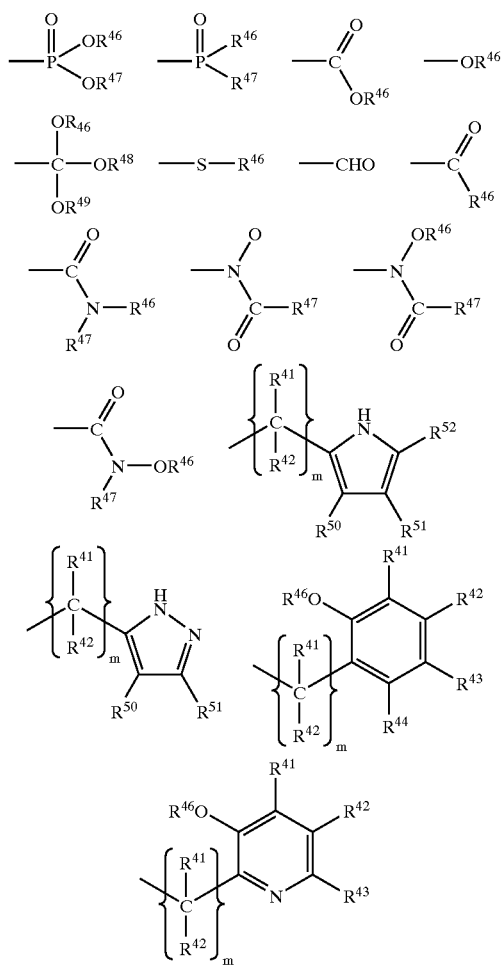

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^1$, $R^2$, $R^3$ and $R^4$ are combined to form a ring structure;

and dimers of Formula I, said dimers being formed by the covalent attachment of two complexing agents of Formula I through a linking group having from 1 to 6 carbon atoms; and physiological salts thereof;

with the proviso that the molecular weight of said complexing agent does not exceed 2000.

4. The method of claims 1 or 2 wherein said chelator has the formula (II)

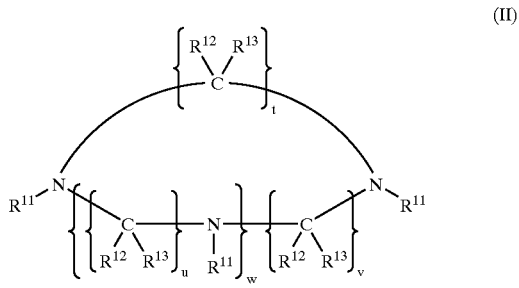

wherein, t, u and v are each independently 2 or 3;

w is an integer of from 1 to 4;

$R^{12}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{11}$ is a member selected from the group consisting of $R^{12}$, $R^{13}$ and radicals of the formula:

(V)

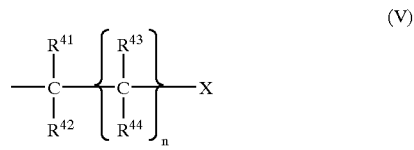

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

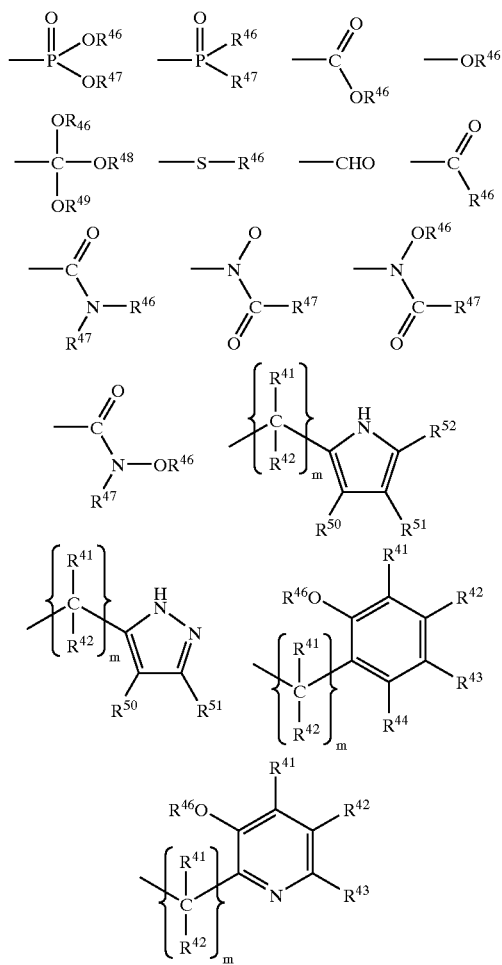

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^{11}$, $R^{12}$, and $R^{13}$ are combined to form a ring structure;

and dimers of Formula II, said dimers being formed by the covalent attachment of two complexing agents of Formula II through a linking group having from 1 to 6 carbon atoms; and physiological salts thereof;

with the proviso that the molecular weight of said complexing agent does not exceed 2000.

5. The method of claims 1 or 2 wherein said chelator has the formula

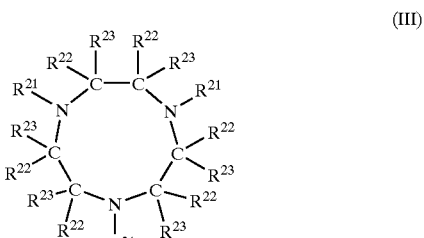

(III)

wherein, $R^{22}$ and $R^{23}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{21}$ is a member selected from the group consisting of $R^{22}$, $R^{23}$ and radicals of the formula:

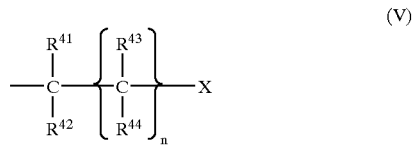

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

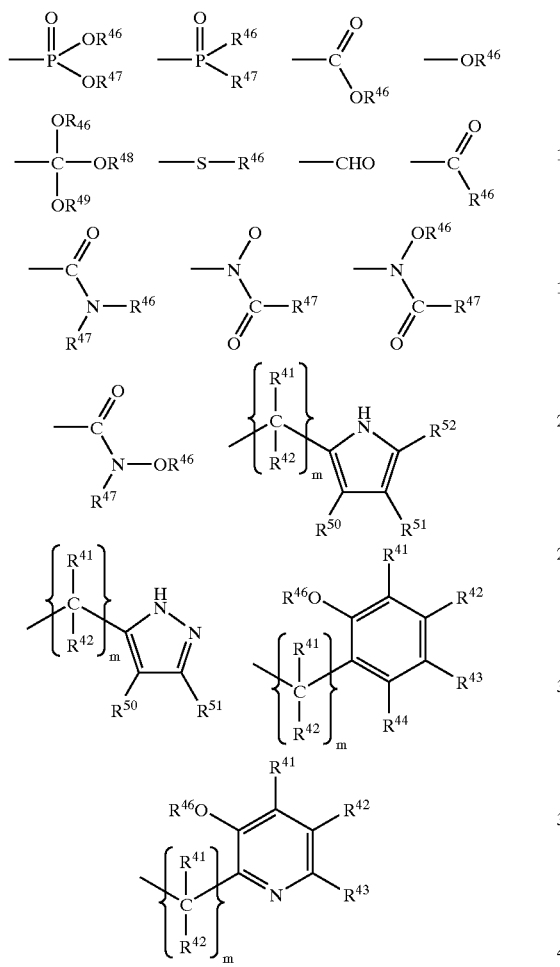

wherein,
$R^{41}$, $R^{42}$, $R^{43}$ and $R^{44}$ are each independently as defined above;
$R^{46}$ and $R^{47}$ are each independently selected from the group consisting of H, alkyl and aryl, or taken together form a ring structure;
$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;
$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and
m is an integer of from 1 to 3 and wherein, optionally, any two of $R^{21}$, $R^{22}$, and $R^{23}$ are combined to form a ring structure;
and dimers of Formula III, said dimers being formed by the covalent attachment of two complexing agents of Formula III through a linking group having from 1 to 6 carbon atoms; and physiological salts thereof;
with the proviso that the molecular weight of said complexing agent does not exceed 2000.

6. The method of claims 1 or 2 wherein said chelator has the formula

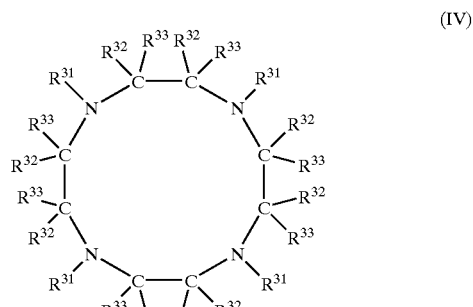

(IV)

wherein,
$R^{32}$ and $R^{33}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{31}$ is a member selected from the group consisting of $R^{32}$, $R^{33}$ and radicals of the formula:

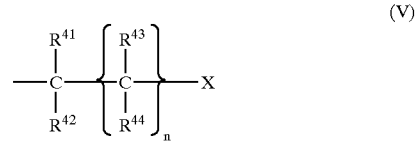

(V)

wherein,
$R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;
n is zero or 1; and
X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

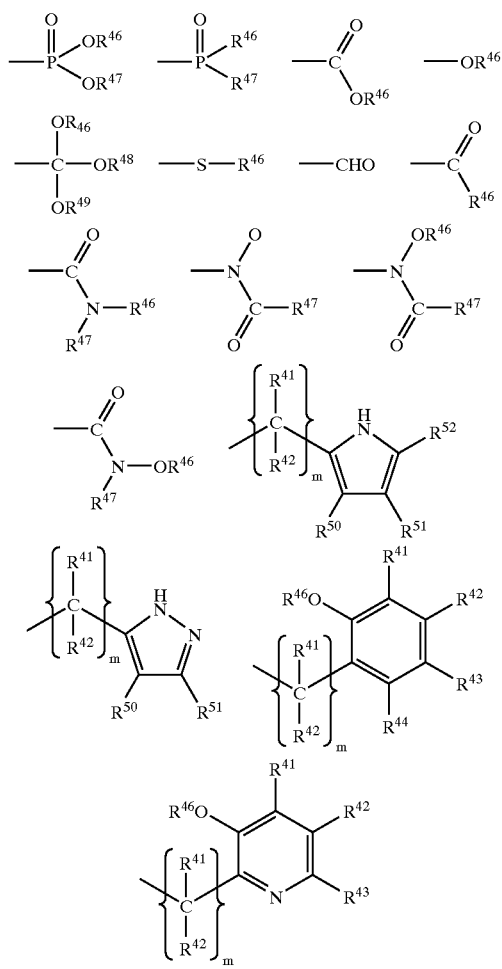

wherein,

R$^{41}$, R$^{42}$, R$^{43}$ and R$^{44}$ are each independently as defined above;

R$^{46}$ and R$^{47}$ are each independently selected from the group consisting of H, alkyl and aryl, or taken together form a ring structure;

R$^{48}$ and R$^{49}$ are each independently selected from the group consisting of H, alkyl, aryl, alkoxy, alkyl interrupted by oxa, aryloxyalkyl, alkoxyaryl, and halogen-substituted versions thereof;

R$^{50}$, R$^{51}$ and R$^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of R$^{31}$, R$^{32}$, and R$^{33}$ are combined to form a ring structure;

and dimers of Formula IV, said dimers being formed by the covalent attachment of two complexing agents of Formula IV through a linking group having from 1 to 6 carbon atoms; and physiological salts thereof;

with the proviso that the molecular weight of said complexing agent does not exceed 2000.

7. The method of claims 1 or 2 wherein said said chelator is a member selected from the group consisting of N,N',N''-tris-(dihydroxyphosphorylmethyl)-triazacyclononane and physiological salts of N,N',N''-tris(dihydroxyphosphorylmethyl)-triazacyclononane.

\* \* \* \* \*